US012006302B2

(12) United States Patent
Andrés-Gil et al.

(10) Patent No.: US 12,006,302 B2
(45) Date of Patent: Jun. 11, 2024

(54) TAU PET IMAGING LIGANDS

(71) Applicant: Janssen Pharmaceutica NV, Beerse (BE)

(72) Inventors: José Ignacio Andrés-Gil, Madrid (ES); Guy Maurits R. Bormans, Rotselaar (BE); Lieven Denis Herwig Declercq, Bierbeek (BE); Katleen Fierens, Antwerp (BE); Joseph Elisabeth Leenaerts, Rijkovorsel (BE); Diederik Willem Elisabeth Moechars, Rotselaar (BE); Frederik Jan Rita Rombouts, Wilrijk (BE); Hartmuth Kolb, San Diego, CA (US); Wei Zhang, San Diego, CA (US)

(73) Assignee: Janssen Pharmaceutica NV, Beerse (BE)

(*) Notice: Subject to any disclaimer, the term of this patent is extended or adjusted under 35 U.S.C. 154(b) by 254 days.

(21) Appl. No.: 17/450,212

(22) Filed: Oct. 7, 2021

(65) Prior Publication Data
US 2022/0024896 A1  Jan. 27, 2022

Related U.S. Application Data

(62) Division of application No. 16/318,287, filed as application No. PCT/EP2017/067898 on Jul. 14, 2017, now Pat. No. 11,168,068.

(60) Provisional application No. 62/363,452, filed on Jul. 18, 2016.

(30) Foreign Application Priority Data

Dec. 15, 2016 (EP) .................................. 16204242
Jan. 18, 2017 (EP) .................................. 17152062

(51) Int. Cl.
*C07D 401/12* (2006.01)
*A61K 51/04* (2006.01)
*C07B 59/00* (2006.01)

(52) U.S. Cl.
CPC ........ *C07D 401/12* (2013.01); *A61K 51/0455* (2013.01); *C07B 59/002* (2013.01); *A61K 2123/00* (2013.01)

(58) Field of Classification Search
CPC .............................. A61K 51/04; C07D 403/00
See application file for complete search history.

(56) References Cited

U.S. PATENT DOCUMENTS

| | | | |
|---|---|---|---|
| 5,480,883 A | 1/1996 | Spada | |
| 5,977,146 A | 11/1999 | Mueller | |
| 6,060,607 A | 5/2000 | Brands | |
| 6,329,205 B1 | 12/2001 | Diwu | |
| 9,108,919 B2 * | 8/2015 | Roux | C07D 403/12 |
| 2003/0187026 A1 | 10/2003 | Li et al. | |
| 2003/0199511 A1 | 10/2003 | Li | |
| 2004/0186114 A1 | 9/2004 | Cirillo | |
| 2007/0254907 A1 | 11/2007 | Bowles | |
| 2008/0264488 A1 | 10/2008 | Balasubramanian | |
| 2009/0023729 A1 | 1/2009 | Nakamura | |
| 2009/0053192 A1 | 2/2009 | Millan | |
| 2009/0259044 A1 | 10/2009 | Kazantsev | |
| 2013/0225527 A1 | 8/2013 | Wang | |
| 2013/0225528 A1 | 8/2013 | Wang | |
| 2013/0343992 A1 | 12/2013 | Black | |
| 2015/0221878 A1 | 8/2015 | Rai | |
| 2016/0244411 A1 | 8/2016 | Kudo et al. | |

FOREIGN PATENT DOCUMENTS

| | | |
|---|---|---|
| CN | 102850156 A | 1/2013 |
| CN | 105481723 A | 4/2013 |
| CN | 103242225 A | 8/2013 |
| CN | 103265480 A | 8/2013 |
| CN | 103965049 A | 8/2014 |
| CN | 104163772 A | 11/2014 |
| CN | 104292096 A | 1/2015 |
| CN | 103265480 B | 10/2015 |
| CN | 102850156 B | 12/2015 |
| CN | 103242225 B | 1/2016 |
| CN | 105315199 A | 2/2016 |
| CN | 105669542 A | 6/2016 |
| CN | 105693631 A | 6/2016 |
| CN | 104649945 8 | 2/2017 |
| CN | 105481723 B | 8/2017 |
| DE | 3112415 A1 | 10/1982 |
| DE | 4228792 A1 | 3/1994 |
| DE | 19545878 A1 | 6/1997 |

(Continued)

OTHER PUBLICATIONS

Ander Wimo et al, The worldwide economic impact of dementia 2010, Alzheimer's & Dementia, 2013, pp. 1-11, 9.

Bennacef, et al ., Discovery and first-in-human evaluation of the lau-imagine pet radiotracer [18 F ] MK-6240, The Journal of Alzheimer's association, 2016, p. 136, Page Number.

Casteels, et al ., Construction and Evaluation of Multitracer Small-Animal PET Probabilistic Allases For Voxel-Based Functional Mapping Of The Rat Brain, The Journal of Nuclear Medicine, 2006, pp. 1858-1866, vol. 47 Issue.

(Continued)

*Primary Examiner* — Michael G. Hartley
*Assistant Examiner* — Jagadishwar R Samala
(74) *Attorney, Agent, or Firm* — Ice Miller LLP

(57) ABSTRACT

The present invention relates to novel, selective radiolabelled tau ligands which are useful for imaging and quantifying tau aggregates, using positron-emission tomography (PET). The invention is also directed to compositions comprising such compounds, to processes for preparing such compounds and compositions, to the use of such compounds and compositions for imaging a tissue or a subject, in vitro or in vivo, and to precursors of said compounds.

2 Claims, 15 Drawing Sheets

(56) References Cited

FOREIGN PATENT DOCUMENTS

| | | |
|---|---|---|
| DE | 19740785 A1 | 8/1998 |
| DE | 10060412 A1 | 6/2002 |
| DE | 10313319 A1 | 10/2004 |
| DE | 102005053541 A1 | 11/2005 |
| DE | 102008010661 A1 | 2/2008 |
| EA | 0468695 B1 | 9/1996 |
| EP | 0468695 A1 | 1/1992 |
| EP | 0512899 A1 | 11/1992 |
| EP | 0827135 A1 | 3/1998 |
| EP | 1847536 A1 | 10/2007 |
| EP | 1873238 B1 | 4/2009 |
| EP | 2651899 81 | 5/2017 |
| JP | 1998/087629 A | 4/1998 |
| JP | 1998/142753 A | 5/1998 |
| JP | 1998/186598 A | 7/1998 |
| JP | 1999/292835 A | 10/1999 |
| JP | 11292835 A | 10/1999 |
| JP | 2000267241 | 9/2000 |
| JP | 2001249432 A | 9/2001 |
| JP | 2001324782 A | 11/2001 |
| JP | 2009051827 A | 3/2009 |
| JP | 2009051828 A | 3/2009 |
| JP | 2009212473 A | 9/2009 |
| JP | 2010087629 A | 4/2010 |
| JP | 2010142753 A | 7/2010 |
| JP | 2010186598 A | 8/2010 |
| JP | 2011512534 A | 4/2011 |
| JP | 2012215687 A | 11/2012 |
| JP | 2012529493 A | 11/2012 |
| JP | 2013020223 A | 1/2013 |
| JP | 2014502601 A | 2/2014 |
| JP | 2016069380 | 5/2016 |
| KR | 20150104865 A | 9/2015 |
| WO | 9220642 A1 | 11/1992 |
| WO | 9618616 A1 | 6/1996 |
| WO | 9706157 A1 | 2/1997 |
| WO | 9724328 A1 | 7/1997 |
| WO | 9842687 A1 | 10/1998 |
| WO | 0064888 A1 | 11/2000 |
| WO | 01/64206 A2 | 9/2001 |
| WO | 2002/20500 A2 | 3/2002 |
| WO | 0250045 A1 | 6/2002 |
| WO | 02059099 A1 | 8/2002 |
| WO | 02068417 A3 | 11/2002 |
| WO | 03013523 A1 | 2/2003 |
| WO | 2003/030909 A1 | 4/2003 |
| WO | 2003/051366 A2 | 6/2003 |
| WO | 0230357 A9 | 10/2003 |
| WO | 2004046133 A1 | 6/2004 |
| WO | 2004009017 A3 | 7/2004 |
| WO | 2004069831 A1 | 8/2004 |
| WO | 03077727 A3 | 9/2004 |
| WO | 2004085423 A1 | 10/2004 |
| WO | 2004098607 A1 | 11/2004 |
| WO | 2005051964 A1 | 6/2005 |
| WO | 2005/123703 | 12/2005 |
| WO | 2005085207 A3 | 3/2006 |
| WO | 2006051311 A1 | 5/2006 |
| WO | 2006065479 A3 | 8/2006 |
| WO | 2006084338 A1 | 8/2006 |
| WO | 2006128172 A2 | 11/2006 |
| WO | 2007/014925 A1 | 2/2007 |
| WO | 2007042906 A1 | 4/2007 |
| WO | 2007008541 A3 | 7/2007 |
| WO | 2007088999 A1 | 8/2007 |
| WO | 2007124546 A1 | 11/2007 |
| WO | 2008017710 A1 | 2/2008 |
| WO | 2008020203 A1 | 2/2008 |
| WO | 2008024961 A1 | 2/2008 |
| WO | 2008049806 A1 | 5/2008 |
| WO | 2008/082487 A2 | 7/2008 |
| WO | 2007072158 A8 | 8/2008 |
| WO | 2008024978 A3 | 8/2008 |
| WO | 2008099073 A1 | 8/2008 |
| WO | 2008103615 A1 | 8/2008 |
| WO | 2006128129 A3 | 10/2008 |
| WO | 2008024970 A3 | 10/2008 |
| WO | 2008122837 A3 | 12/2008 |
| WO | 0230358 A3 | 6/2009 |
| WO | 2008119015 A3 | 9/2009 |
| WO | 2009070579 A3 | 9/2009 |
| WO | 2010007756 A1 | 1/2010 |
| WO | 2010026095 A1 | 3/2010 |
| WO | 2010057833 A1 | 5/2010 |
| WO | 2010075561 A1 | 7/2010 |
| WO | 2010094289 A1 | 8/2010 |
| WO | 2010143168 A2 | 12/2010 |
| WO | 2011016472 A1 | 2/2011 |
| WO | 2010072696 A9 | 6/2011 |
| WO | 2010143168 A3 | 6/2011 |
| WO | 2010143170 A3 | 8/2011 |
| WO | 2011083998 A3 | 10/2011 |
| WO | 2010143169 A3 | 11/2011 |
| WO | 2010129053 A8 | 12/2011 |
| WO | 2011157688 A1 | 12/2011 |
| WO | WO 2010143168 * | 12/2011 |
| WO | 2011113060 A3 | 1/2012 |
| WO | 2011133729 A3 | 3/2012 |
| WO | 2012052540 A1 | 4/2012 |
| WO | 2012074050 A1 | 6/2012 |
| WO | 2012068335 A3 | 7/2012 |
| WO | 2012079032 A3 | 9/2012 |
| WO | 2012155022 A1 | 11/2012 |
| WO | 2013017479 A1 | 2/2013 |
| WO | 2013017480 A1 | 2/2013 |
| WO | 2013097518 A1 | 7/2013 |
| WO | 2013154710 A1 | 10/2013 |
| WO | 2014015936 A1 | 1/2014 |
| WO | 2014065209 A1 | 5/2014 |
| WO | 2014121883 A1 | 8/2014 |
| WO | 2014094965 A3 | 11/2014 |
| WO | 2014181287 A1 | 11/2014 |
| WO | 2014187297 A1 | 11/2014 |
| WO | 2014187298 A1 | 11/2014 |
| WO | 2014207100 A1 | 12/2014 |
| WO | 2015001518 A1 | 1/2015 |
| WO | 2015051458 A1 | 4/2015 |
| WO | 2015060365 A1 | 4/2015 |
| WO | 2015078799 A1 | 6/2015 |
| WO | 2013184755 A3 | 7/2015 |
| WO | 2015061247 A3 | 7/2015 |
| WO | 2015110263 A1 | 7/2015 |
| WO | 2015120800 A1 | 8/2015 |
| WO | 2015140572 A1 | 9/2015 |
| WO | 2015157556 A1 | 10/2015 |
| WO | 2016022645 A1 | 2/2016 |
| WO | 2016071283 A1 | 5/2016 |
| WO | 2016109880 A1 | 7/2016 |
| WO | 2016135053 A1 | 9/2016 |
| WO | 2016176657 A1 | 11/2016 |
| WO | 2016196816 A1 | 12/2016 |
| WO | 2017114510 A1 | 7/2017 |

OTHER PUBLICATIONS

Cheng, et al., Relationship between the inhibition Constant (KI) and the Concentration of inhibitor which causes 50 per cent Inhibition (I50) of an enzymatic reaction, Biochemical Pharmacology, 1973, pp. 3099-3108, vol. 22.

Clayton A. Wiley et al, Carbon 11-Labeled Pittsburgh Compound B and Carbon 11-Labeled (R)-PK11195 Positron Emission Tomographic Imaging in Alzheimer Disease, Archives of Neurology, Jan. 2009, pp. 60-67, 66.

David T. Chien, Early Clinical PET Imaging Results with the Novel PHF-Tau Radioligand [F18]-T808, Journal of Alzheimer's Disease, Jan. 7, 2013, pp. 171-184, 38.

Dean F. Wong et al, In Vivo Imaging of Amyloid Deposition in Alzheimer's Disease Using the Radioligand 18F-AV-45 (Flobetapir F 18), Journal of Nuclear Medicine, Jan. 5, 2010, pp. 913-920, 51.

Declercq, et al ., Preclinical Evaluation of 18F-JNJ64349311, a Novel PET Tracer for Tau Imaging, J Nucl Med, 2017, pp. 975-981, vol. 58.

(56) References Cited

OTHER PUBLICATIONS

Eric D. Hostetler et al, Preclinical Characterization of 18F-MK-6240, a Promising PET Tracer for In Vivo Quantification of Human Neurofibrillary Tangles, J Nucl Med, May 26, 2016, pp. 1599-1606, 57.
Fodero-Tavolett, et al ., Assessing THK523 selectivity for tau deposits in Alzheimer's disease and non-Alzheimer's disease tauopathies, Alzheimer's Research & Therapy, 2014, pp. 1-10, vol. 6 Issue 11.
Frydman, et al., Synthesis of Substituted 1,5- and 1,7-Naphtyridines and Related Lactams, J.Org. Chem., 1971, pp. 450-454, vol. 36 Issue 3.
Greenberg, et al., A preparation of Alzheimer paired helical filaments that displays distinct T proteins by polyacrylamide gel electrophoresis, Proc. Natl. Acad. Sci, Apr. 27, 1990, pp. 5827-5831, vol. 87.
Hosteler, et al., Preclinical Characterization of 18F-MK-6240, a promising PET Tracer for In Vivo Quantification of Human Neurofibrillary Tangles, The journal of nuclear medicine, 2016, pp. 1599-1606, vol. 57 Issue 10.
J. Biernat et al., The switch of tau protein to an Alzheimer-like state includes the phosphorylation of two serine—proline motifs upstream of the microtubule binding region, The EMBO Journal, Jan. 21, 1992, pp. 1593-1597, vol. 11 No. 4.
Johnson, et al ., Tau Positron Emission Tomographic Imaging in Aging and Early Alzheimer Disease, Ann Neurol, 2015, pp. 110-119, vol. 79.
Kjell Nagren et al, Radiopharmaceuticals for positron emission tomography investigations of Alzheimer's disease, Eur J Nucl Med Mol Imaging, Dec. 22, 2009, pp. 1575-1593, 37.
Kok, et al ., Monoamine oxidase B inhibitor, selegiline, reduces 18 F-THK5351 uptake in the human brain, Alzheimers Research & Therapy, 2017, pp. 1-9, vol. 9 Issue 25.
Lieven Declercq, Molecular Imaging, Comparison of New Tau PET-Tracer Candidates With [18F]T808 and [18F] 807, Jan. 27, 2016, 1-15, vol. 15.
Manuela Ariza, Journal of Medicinal Chemistry, Tau Positron Emission Tomography (PET) Imaging: Past, Present, and Future, Jun. 11, 2015, 4365-4382, vol. 58 No. 11.
Marquie, et al ., Validating Novel Tau Positron Emission Tomography Tracer [F-18]-AV-1451 (T807) on Postmortem Brain Tissue, Ann Neurol, 2015, pp. 787-800, vol. 78 Issue 5.
NCT01457677, View of NCT01457677 on Feb. 18, 2014, ClinicalTrials.gov Archive, Feb. 18, 2014, pp. 1-3, not applicable.
Okamura, et al ., Advances in the development of tau PET radiotracers and their clinical applications, Ageing Research Reviews, 2016, pp. 1-7, vol. 30.
Ossenkoppele, et al ., Tau, Amyloid, and Hypometabolism in a Patient with Posterior Cortical Atrophy, Ann Neurol, 2015, pp. 338-342, vol. 77 Issue 2.
Walji, et al ., Discovery of 6-(Fluoro- 18F)-3-(1 H-pyrrolo[2,3-c]pyridin-1yl)isoquinolin-5-amine ([ 18 F]-MK-6240): A Positron Emission Tomography (PET) Imaging Agent for Quantification of Neurofibrillary Tangles (NFTs), Journal of medicinal chemistry, 2016, pp. 4778-4789, vol. 59.
Zhang, et al ., A Highly Selective and Specific PET Tracer for Imaging of Tau Pathologies, Journal of Alzheimer's Disease, 2012, pp. 601-612, vol. 31 Issue 3.
Lisheng Cai et al., Chemsitry with [18F]Fluoride Ion, Eir. J. Org. Chem, 2853-2873. (Year: 2008).
Rombouts, Frederik J.R., et al., "Discovery of N-(Pyridin-4-yl)-1,5-naphthyridin-2-amines as Potential Tau Pathology PET Tracers for Alzheimer's Disease," Journal of Medicinal Chemistry, vol. 60 (4), pp. 1272-1291, (2017).

* cited by examiner

FIG. 4
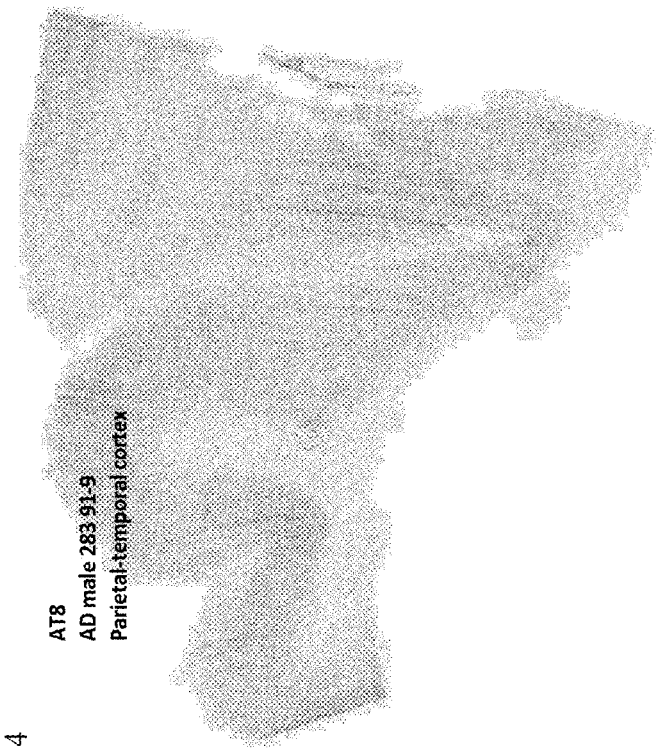
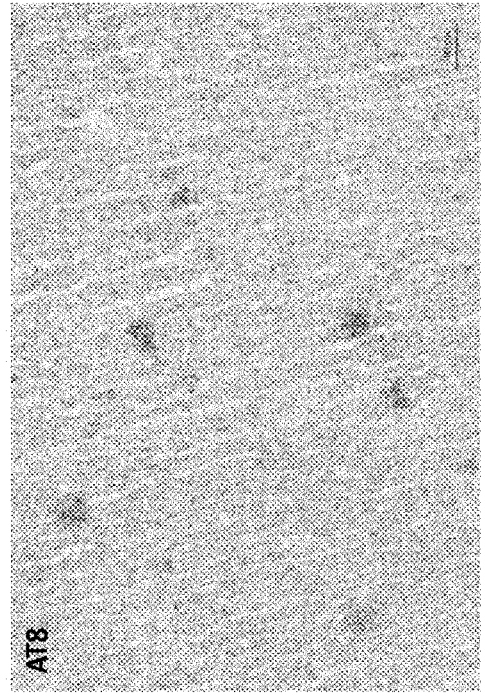
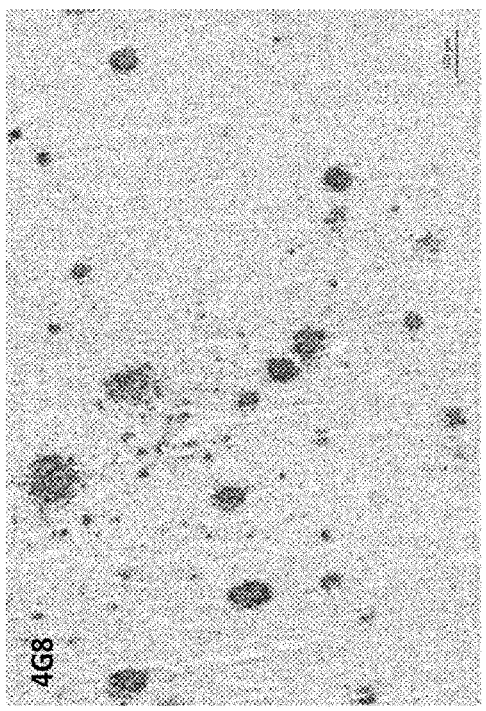

FIG. 6
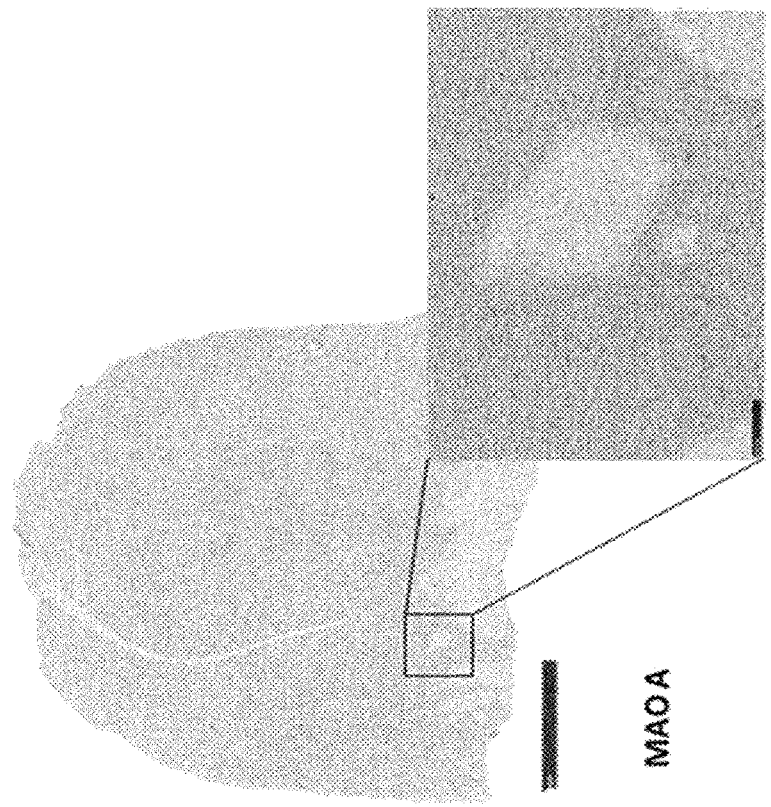
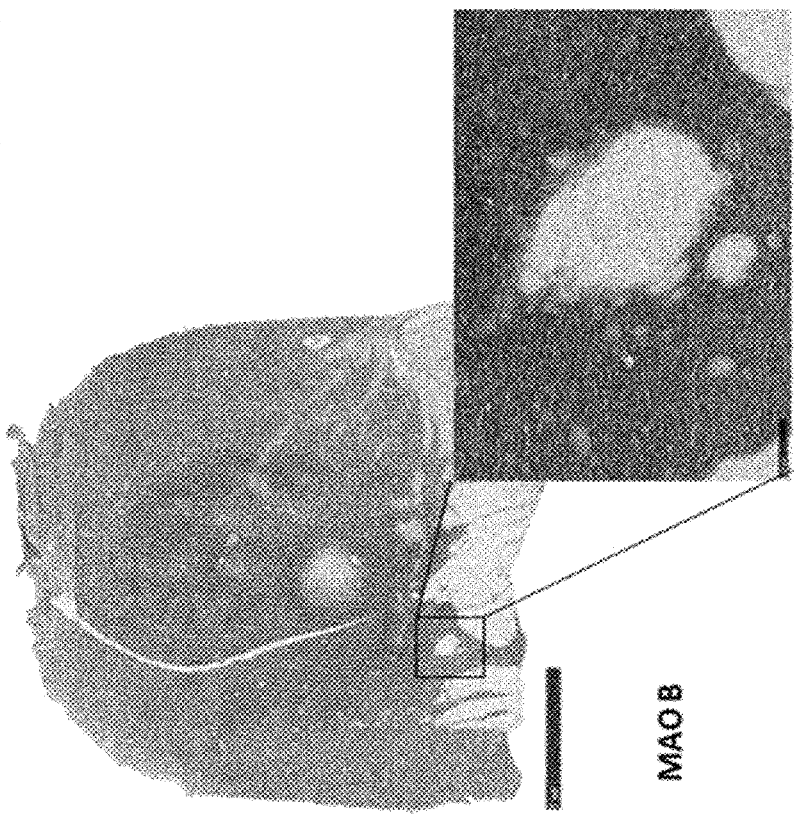

TAU PET IMAGING LIGANDS

CROSS-REFERENCE TO RELATED APPLICATION

This application is a divisional application of U.S. patent application Ser. No. 16/318,287 filed Jan. 16, 2019 which is a Section 371 of International Application No. PCT/EP2017/067898 filed Jul. 14, 2017, which was published in the English language Jan. 25, 2018, under International Publication No. WO 2018/015307 A1, which claims priority to European Application No. EP17152062.0 filed Jan. 18, 2017, European Application No. EP16204242.8 filed Dec. 15, 2016 and U.S. Provisional Application No. 62/363,452 filed Jul. 18, 2016, the disclosures of which are incorporated herein by reference in their entireties.

FIELD OF THE INVENTION

The present invention relates to novel, selective radiolabelled tau ligands which are useful for imaging and quantifying tau aggregates, using positron-emission tomography (PET). The invention is also directed to compositions comprising such compounds, to processes for preparing such compounds and compositions, to the use of such compounds and compositions for imaging a tissue or a subject, in vitro or in vivo, and to precursors of said compounds.

BACKGROUND OF THE INVENTION

Alzheimer's Disease (AD) is a neurodegenerative disease associated with aging. AD patients suffer from cognition deficits and memory loss as well as behavioural problems such as anxiety. Over 90% of those afflicted with AD have a sporadic form of the disorder while less than 10% of the cases are familial or hereditary. In the United States, about one in ten people at age 65 have AD while at age 85, one out of every two individuals are afflicted by AD. The average life expectancy from the initial diagnosis is 7-10 years, and AD patients require extensive care either in an assisted living facility or by family members. With the increasing number of elderly in the population. AD is a growing medical concern. Currently available therapies for AD merely treat the symptoms of the disease but not the underlying pathology causing the disease.

The hallmark pathological features in the brain of AD patients are neurofibrillary tangles which are generated by aggregates of hyperphosphorylated tau protein and amyloid plaques which form by aggregation of beta-amyloid peptide. Though the most prevalent neurodegenerative disorder is AD, aggregated tau protein is also a characteristic of other neurodegenerative diseases known as "tauopathies", which additionally but not exclusively include tangle-only dementia (TD), argyrophilic grain disease (AGD), progressive supranuclear palsy (PSP), corticobasal degeneration (CBD), Pick disease (PiD), and frontotemporal dementia and parkinsonism linked to chromosome 17 (FTDP-17). The heterogeneity of these disorders is closely related to the wide range of human tau isoforms and post-translational modifications. Tau aggregates may appear ultrastructurally as paired helical filaments (PHF), straight filaments (SF), randomly coiled filaments (RCF), or twisted filaments (TF); this variability translates into polymorphism. A correlation of neurofibrillary tangles has been made with the level of cognitive impairment in AD and/or the chance of developing AD. However, diagnosis can still only be performed postmortem by means of biopsy/autopsy. Examination based on history and statistical memory testing require clear evidence of impairment or dementia, and are often inaccurate or insensitive, and measurement of Aβ peptides and total tau proteins in cerebrospinal fluid by lumbar puncture is invasive and amenable to adverse effects. Apart from the intrinsic complexity of AD, the development of a cure has been hampered by the lack of reliable tools for early diagnosis, staging, and accurately monitoring disease progression. There is therefore still a need to identify a means to perform diagnosis and/or monitor disease progression. Imaging of tau aggregates may provide such means, particularly when anti-tau treatments emerge.

Positron Emission Tomography (PET) is a non-invasive imaging technique that offers the highest spatial and temporal resolution of all nuclear imaging techniques and has the added advantage that it can allow for true quantification of tracer concentrations in tissues. It uses positron emitting radionuclides for detection.

Several positron emission tomography radiotracers have been reported so far for imaging of tau aggregates (for a review, see for instance Ariza et al. *J. Med Chem.* 2015, 58, 4365-4382). "Preclinical Characterization of $^{18}$F-MK-6240, a promising PET Tracer for In Vivo Quantification of Human Neurofibrillary Tangles" in J. Nucl. Med 2016; 57: 1599-1610 disclose 6-fluoro-3-(1H-pyrrolo[2,3-c]pyridine-1-yl)isoquinoline-5-amine which binds with high affinity to human AD brain cortex homogenates containing abundant NFT but binds poorly to amyloid plaque-rich, NFT-poor AD brain homogenates. Moderate defluorination is observed with $^{18}$F-MK-6240 as skull uptake. The article "Radiopharmaceuticals for positron emission tomography investigations of Alzheimer's disease" in Eur. J. Nucl. Med. Imaging 2010; 37(8): 1575-1593 reports on an isoquinoline compound [$^{11}$C]PK11195 which binds to peripheral cortical benzodiazepine receptors in activated microglia and which was further reported in "Carbon 11-labeled Pittsburgh compound B and carbon 11-labeled (R)-PK11195 positron emission tomographic imaging in Alzheimer's disease in Arch. Neurol. 2009; 66(1): 60-67 as failing to show any differences in brain retention between patients and healthy volunteers. PET imaging of the human brain with the quinoline compound $^{18}$F-THK5351 having high affinity to PHF was shown to be confounded by off-target binding to the enzyme monoamine oxidase MAO-B (Alzheimer's Research & Therapy 2017; 9; 25 DOI 10.1186/s13195-017-0253-y).

There is still a need to provide selective, improved positron emission tomography radiotracers for imaging tau aggregates with a good balance of properties including, but not limited to, high affinity and selectivity towards tau aggregates, reversible binding, permeability, suitable brain pharmacokinetic profile, i.e. rapid distribution throughout the brain, rapid clearance, minimal non-specific binding, and synthetic accessibility.

SUMMARY OF THE INVENTION

It is therefore an object of the present invention to provide isoquinoline-6-amine compounds useful as tau PET radiotracers. Therefore, in one aspect, the present invention relates to a compound having the Formula (I)

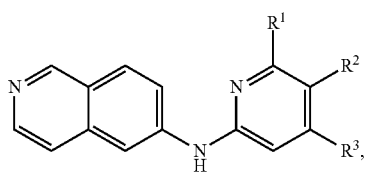

(I)

wherein
at least one atom is radioactive, and wherein
R² is methyl, and either R¹ is F and R³ is H, or R¹ is H and R³ is F; or
R¹ and R³ are both H, and R² is selected from the group consisting of —C$_{1-4}$alkyl-F, —OC$_{1-4}$alkyl-F, and —NR⁴—C$_{1-4}$alkyl-F, wherein R⁴ is H or methyl;
or a pharmaceutically acceptable salt or a solvate thereof.
In particular, the present invention relates to a compound of Formula (I')

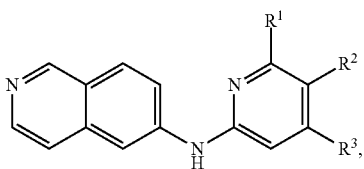

(I')

wherein
R² is methyl, and either R¹ is ¹⁸F and R³ is H, or R¹ is H and R³ is ¹⁸F; or
R¹ and R³ are both H, and R² is selected from the group consisting of —C$_{1-4}$alkyl-¹⁸F, —OC$_{1-4}$alkyl-¹⁸F, and —NR⁴—C$_{1-4}$alkyl-¹⁸F, wherein R⁴ is H or methyl;
or a pharmaceutically acceptable salt or a solvate thereof.

In another aspect, the invention relates to precursor compounds for the synthesis of the compounds of Formula (I) or (I'), as previously defined. Thus, the present invention also relates to a compound of Formula (P-1)

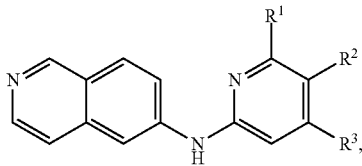

(P-1)

wherein
R² is methyl, and either R¹ is selected from the group consisting of Br, —NO₂, —[N(CH₃)₃]⁺, and 4-CH₃-Ph-SO₂—O—, and R³ is H, or R is H and R³ is selected from the group consisting of Br, —NO₂, —[N(CH₃)₃]⁺, and 4-CH₃-Ph-SO₂—O—; or
R¹ and R³ are both H, and R² is selected from the group consisting of —C$_{1-4}$alkyl-Br, —C$_{1-4}$alkyl-I, —C$_{1-4}$alkyl-O—SO₂CH₃, 4-CH₃-Ph-SO₂—O—C$_{1-4}$alkyl-, —C$_{1-4}$alkyl-OH, —OC$_{1-4}$alkyl-Br, —OC$_{1-4}$alkyl-I, —OC$_{1-4}$alkyl-O—SO₂CH₃, 4-CH₃-Ph-SO₂—O—C$_{1-4}$alkyl-O—, —OC$_{1-4}$alkyl-OH, —NR⁴—C$_{1-4}$alkyl-Br, —NR⁴—C$_{1-4}$alkyl-I, —NR⁴—C$_{1-4}$alkyl-O—SO₂CH₃, 4-CH₃-Ph-SO₂—O—C$_{1-4}$alkyl-NR⁴—, and —NR⁴—C$_{1-4}$alkyl-OH, wherein R⁴ is H or methyl;
or a pharmaceutically acceptable salt or a solvate thereof.

In compounds of Formula (P-1), when either of R¹ or R³ are —[N(CH₃)₃]⁺, suitable anionic counterions include, but are not limited to trifluoroacetate (—[OC(O)CF₃]⁻), an organic sulfonate (e.g. C$_{1-4}$alkylsulfonate, or phenylsulfonate wherein the phenyl may be optionally substituted with a C$_{1-4}$alkyl, halo, or a nitro group) and tartrate. Particular examples of C$_{1-4}$alkylsulfonate include methanesulfonate (mesylate), 4-methylbenzenesulfonate (tosylate), 4-bromobenzensulfonate and 4-nitrobenzenesulfonate. In particular the anionic counterion is selected from trifluoroacetate, tosylate, and mesylate.

The invention also relates to the reference materials of compounds of Formula (I) or (I'), corresponding to the corresponding non-radiolabelled compounds, herein referred to as compounds of Formula [¹⁹F]-(I)

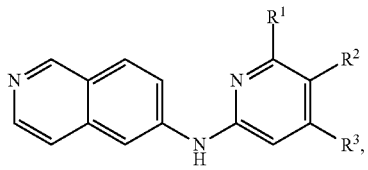

[¹⁹F]-(I)

wherein
R² is methyl, and either R¹ is F and R³ is H, or R¹ is H and R³ is F; or
R¹ and R³ are both H, and R² is selected from the group consisting of —C$_{1-4}$alkyl-F, —OC$_{1-4}$alkyl-F, and —NR⁴—C$_{1-4}$alkyl-F, wherein R⁴ is H or methyl;
or a pharmaceutically acceptable salt or a solvate thereof.

The invention also relates to a pharmaceutical composition comprising a compound of Formula (I), in particular a compound of Formula (I'), or a pharmaceutically acceptable salt thereof and a pharmaceutically acceptable carrier or diluent. In particular, said pharmaceutical composition is a diagnostic pharmaceutical composition. Said pharmaceutical composition is in particular, a sterile solution. Thus, illustrative of the invention is a sterile solution comprising a compound of Formula (I), in particular a compound of Formula (I'), as described herein.

The invention further relates to the use of a compound of Formula (I), in particular a compound of Formula (I'), as an imaging agent. Exemplifying the invention is a use of a compound of Formula (I), in particular a compound of Formula (I'), as described herein, for, or a method of, imaging a tissue or a subject, in vitro or in vivo.

In particular, the invention relates to a compound of Formula (I), in particular a compound of Formula (I'), for use in binding and imaging tau aggregates in patients suffering from, or suspected to be suffering from, a tauopathy. Particular tauopathies are, for example, Alzheimer's disease, tangle-only dementia (TD), argyrophilic grain disease (AGD), progressive supranuclear palsy (PSP), corticobasal degeneration (CBD). Pick disease (PiD), and frontotemporal dementia and parkinsonism linked to chromosome 17 (FTDP-17). In particular, the tauopathy is Alzheimer's disease.

The invention further relates to a compound of Formula (I), in particular a compound of Formula (I'), for diagnostic imaging of tau aggregates in the brain of a subject, and to the use of the compound of Formula (I), in particular the compound of Formula (I'), in binding and imaging tau aggregates in patients suffering from, or suspected to be suffering from, a tauopathy. Particular tauopathies are, for example, Alzheimer's disease, tangle-only dementia (TD), argyrophilic grain disease (AGD), progressive supranuclear palsy (PSP), corticobasal degeneration (CBD), Pick disease (PiD), and frontotemporal dementia and parkinsonism linked to chromosome 17 (FTDP-17). In particular, the tauopathy is Alzheimer's disease.

The invention also relates to a method for imaging a tissue or a subject, comprising contacting with or providing or administering a detectable amount of a labelled compound of Formula (I), in particular a labelled compound of Formula (I'), as described herein to a tissue, or a subject, and detecting the compound of Formula (I), in particular the compound of Formula (I').

Further exemplifying the invention is a method of imaging a tissue, or a subject, comprising contacting with or providing to a tissue, or a subject, a compound of Formula (I), in particular a compound of Formula (I'), as described herein, and imaging the tissue, or subject with a positron-emission tomography imaging system.

Additionally, the invention refers to a process for the preparation of a compound of Formula (I'-a) or (I'-b), referred to in particular hereinbelow as (I'-a1), (I'-a2), (I'-b1), (I'-b2), (I'-b3), or a pharmaceutically acceptable salt or a solvate thereof as described herein, comprising
  (a) the step of reacting a compound of Formula (P-a1) or a pharmaceutically acceptable salt or a solvate thereof, as defined herein, with a source of fluoride $^{18}F^-$ under suitable conditions, or
  (b) the step of reacting a compound of Formula (P-a2) or a pharmaceutically acceptable salt or a solvate thereof, as defined herein, with a source of fluoride $^{18}F^-$ under suitable conditions, or
  (c) the step of reacting a compound of Formula (P-b1) or a pharmaceutically acceptable salt thereof, as defined herein, with an activating reagent such as methanesulfonyl chloride or 4-toluenesulfonyl chloride in the presence of a base such as triethylamine or N,N-diisopropylethylamine (DIPEA), and subsequently reacting the resulting methanesulfonate or 4-toluenesulfonate with a source of fluoride $^{18}F^-$ under suitable conditions, or
  (d) the step of reacting a compound of Formula (P-b2) or a pharmaceutically acceptable salt thereof, as defined herein, with an activating reagent such as methanesulfonyl chloride or 4-toluenesulfonyl chloride in the presence of a base such as triethylamine or DIPEA, and subsequently reacting the resulting methanesulfonate or 4-toluenesulfonate with a source of fluoride $^{18}F^-$ under suitable conditions, or
  (e) the step of reacting a compound of Formula (P-b3) or a pharmaceutically acceptable salt thereof, as defined herein, with an activating reagent such as methanesulfonyl chloride or 4-toluenesulfonyl chloride in the presence of a base such as triethylamine or DIPEA, and subsequently reacting the resulting methanesulfonate or 4-toluenesulfonate with a source of fluoride $^{18}F^-$ under suitable conditions.

Typical conditions for the activation of the precursors of Formulae (P-b1), (P-b2) and (P-b3), include for instance, methanesulfonyl chloride as activating agent, dry dimethyl sulfoxide (DMSO) as solvent, at room temperature for a sufficient period of time to drive the reaction to completion, typically, 10 minutes. The skilled person will understand that when $R^4$ is H in (P-b3), the preparation of the compound of Formula (I'-b3) will include the additional steps of protecting the amine functionality with a suitable protecting group, such as for example tert-butyloxycarbonyl (Boc) or alternative suitable amine protecting group, and subsequently cleaving such protecting group, using typically trifluoroacetic acid (TFA) when the protecting group is Boc.

A suitable source of $^{18}F^-$ is, for example 4,7,13,16,21,24-hexaoxa-1,10-diazabicyclo[8.8.8]hexacosane potassium fluoride-[$^{18}F$] (1:1) (also referred to as [$^{18}F$]KF.K222). Suitable conditions include, those appropriate for nucleophilic substitution known in the art, for example, using DMSO or DMF as solvent, in particular DMSO, under conventional heating or microwave irradiation (e.g. 50 W), for example at about 90-160° C., or at about 120-160° C., in particular at about 90 or 160° C., for a sufficient period of time to enable the reaction to proceed to completion, for example 10 min when the reaction is performed under microwave irradiation.

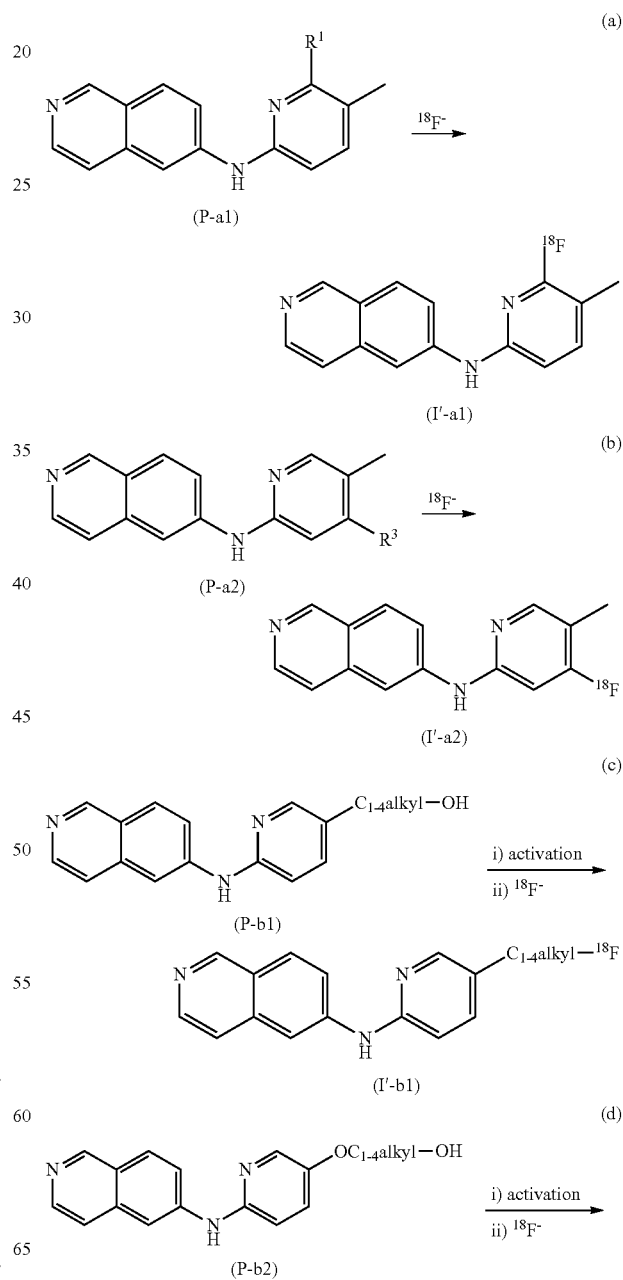

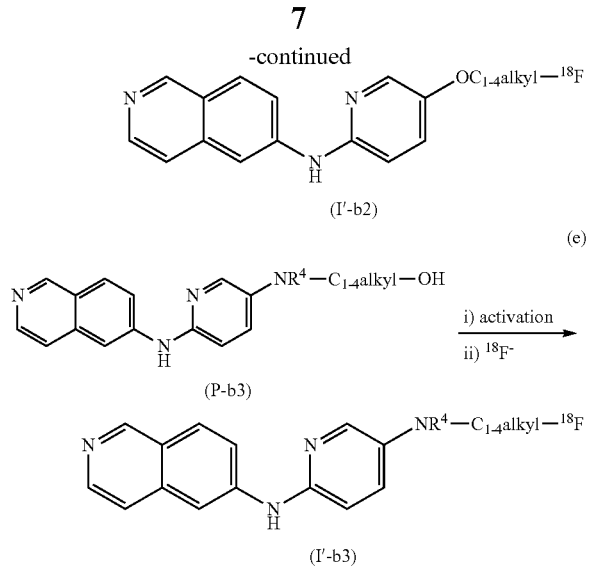

BRIEF DESCRIPTION OF THE FIGURES

FIG. 3D shows incubation with 10 nM [$^3$H]Co. No. 1 on human AD tissue (parietal-temporal cortex, Braak stage VI) having confirmed tau and amyloid pathology by IHC as shown in FIG. 4. FIG. 3E shows incubation with 10 nM [$^3$H]Co. No. 1 on human AD tissue (lateral-occipital gyrus, Braak stage 0), with confirmed amyloid pathology but no tau pathology by IHC as shown in FIG. 5. FIG. 3F shows incubation with 10 nM [$^3$H]THK5351 on human basal ganglia tissue, and treatment with 10 µM Co. No. 1 (G) or 10 µM THK5351 (H). FIG. 3I shows incubation with [$^3$H]THK-5351 on human AD tissue (parietal-temporal cortex, Braak stage VI) with confirmed tau and amyloid pathology as shown in FIG. 4. FIG. 3J shows incubation with 10 nM [$^3$H]THK5351 on human AD tissue (lateral-occipital gyrus, Braak stage 0) with confirmed amyloid pathology but no tau pathology as shown in FIG. 5. FIG. 3K shows incubation with 3 nM [$^3$H]-AV-45 on human basal ganglia (K), the aforementioned human AD tissue containing both amyloid beta and tau pathology (L) and the aforementioned human AD tissue containing amyloid beta but no taupathology (M).

FIG. 4 shows 4G8 and AT8 IHC of amyloid and tau pathology in AD brain slices from parietal-temporal cortex region of the same patient as the slices used for the images in FIG. 3.

FIG. 6 shows IHC confirmation of the expression of MAO-B (left) and MAO-A (right) in the human basal ganglia tissue used for in vitro binding shown in FIG. 3.

DETAILED DESCRIPTION OF THE INVENTION

Figure 1:
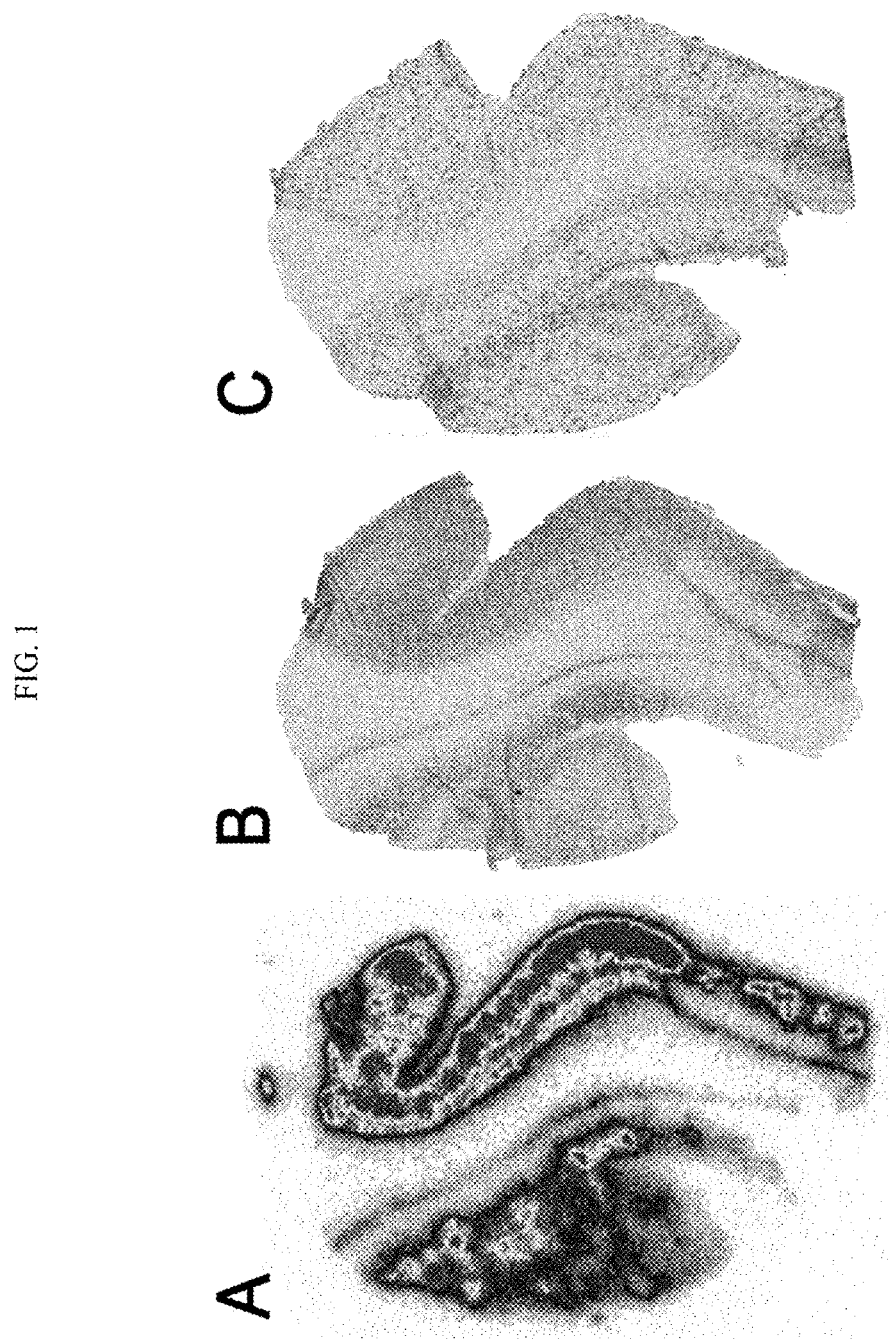
FIG. 1 shows in vitro autoradiography (ARG) using [$^{18}$F]Co. No. 1 (7.4 kBq/500 µL/slice) on a slice of the visual cortex of a patient with AD (Braak stage VI) (A). Adjacent slices were immunostained for tau pathology (B, AT8) and for amyloid beta pathology (C, 4G8).

In an embodiment, the compound of Formula (I) is in particular a compound of Formula (I-a)

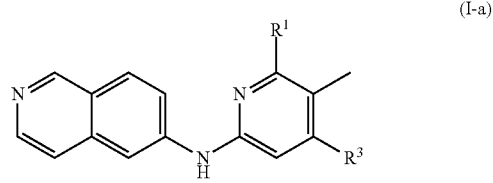

wherein
at least one atom is radioactive, and wherein $R^1$ is F and $R^3$ is H, or $R^1$ is H and $R^3$ is F; or a pharmaceutically acceptable salt or a solvate thereof.

More in particular, the compound of Formula (I) is a compound of Formula (I'-a)

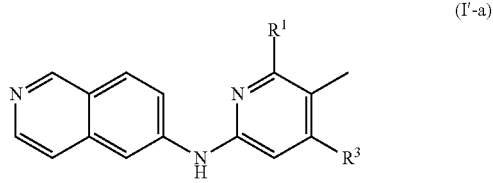

wherein
R$^1$ is $^{18}$F and R$^3$ is H, or R$^1$ is H and R$^3$ is $^{18}$F;
or a pharmaceutically acceptable salt or a solvate thereof.

In another embodiment, the compound of Formula (I) is in particular a compound of Formula (I-b)

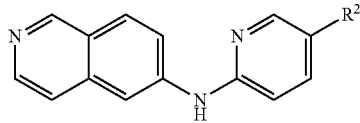

(I-b)

wherein
at least one atom is radioactive, and wherein R$^2$ is selected from the group consisting of —C$_{1-4}$alkyl-F, —OC$_{1-4}$alkyl-F, and —NR$^4$—C$_{1-4}$alkyl-F, wherein R$^4$ is H or methyl; or a pharmaceutically acceptable salt or a solvate thereof.

More in particular, the compound of Formula (I) is a compound of Formula (I'-b)

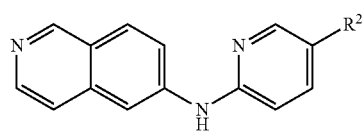

(I'-b)

wherein
R$^2$ is selected from the group consisting of —C$_{1-4}$alkyl-$^{18}$F, —OC$_{1-4}$alkyl-$^{18}$F, and —NR$^4$—C$_{1-4}$alkyl-$^{18}$F, wherein R$^4$ is H or methyl;
or a pharmaceutically acceptable salt or a solvate thereof.

In an embodiment, the compound of Formula (I), in particular of Formula (I'), is

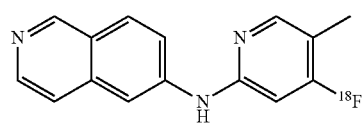 [SMILES: Cc1cnc(Nc2ccc3cnccc3c2)cc1[18F]]

or a pharmaceutically acceptable salt or a solvate thereof.

In another particular embodiment, the precursor compound for the synthesis of the compound of Formula (I) or (I'), as previously defined, is in particular a compound of Formula (P-1)

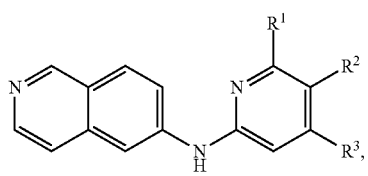

(P-1)

wherein
R$^2$ is methyl, and either R$^1$ is selected from the group consisting of Br, —NO$_2$, —[N(CH$_3$)$_3$]$^+$, and 4-Me-Ph-SO$_2$—O—, and R$^3$ is H, or R$^1$ is H and R$^3$ is selected from the group consisting of Br, —NO$_2$, —[N(CH$_3$)$_3$]$^+$, and 4-Me-Ph-SO$_2$—O—; or R$^1$ and R$^3$ are both H, and R$^2$ is selected from the group consisting of —C$_{1-4}$alkyl-OH, —OC$_{1-4}$alkyl-OH, and —NR$^4$—C$_{1-4}$alkyl-OH, wherein R$^4$ is H or methyl;
or a pharmaceutically acceptable salt or a solvate thereof.

The invention also relates to the reference material corresponding to the non-radiolabelled compound 1, corresponding to the [$^{19}$F]-compound

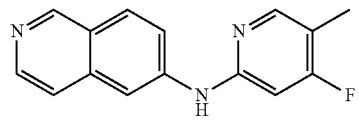 [SMILES: Cc1cnc(Nc2ccc3cnccc3c2)cc1F]

or a pharmaceutically acceptable salt or a solvate thereof.

In another particular embodiment, the compound of Formula [$^{19}$F]-(I) is in particular a compound of Formula [$^{19}$F]-(I-a)

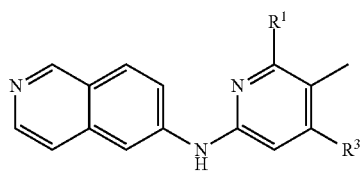

[$^{19}$F]-(I-a)

wherein
R$^1$ is F and R$^3$ is H, or R$^1$ is H and R$^3$ is F;
or a pharmaceutically acceptable salt or a solvate thereof.

In another particular embodiment, the compound of Formula [$^{19}$F]-(I) is in particular a compound of Formula (I-b)

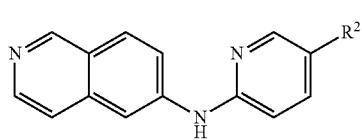

[$^{19}$F]-(I-b)

wherein
R$^2$ is selected from the group consisting of —C$_{1-4}$alkyl-F, —OC$_{1-4}$alkyl-F, and —NR$^4$—C$_{1-4}$alkyl-F, wherein R$^4$ is H or methyl;
or a pharmaceutically acceptable salt or a solvate thereof.

[$^{19}$F]-Co. No. 1 has shown potent binding (pIC$_{50}$ 8.24) to extracted human tau aggregates in a radiolabel displacement assay using an internally made tritium analogue of compound T-808 (T-808 is developed by Siemens, see for example, *J. Alzheimers Dis.* 2014, 38, 171-184), and which is referred to herein as [$^3$H]-T808. In addition, Co. No. 1 shows weak binding to extracted human amyloid-beta aggregates (pIC$_{50}$ 5.18) in a radiolabel displacement assay using an internally made tritium analogue of Florbetapir (also known as Amyvid® from Eli Lilly and Co., or AV-45, see for example, *J. Nucl. Med.* 2010, 51, 913-920), and which is referred to herein as [$^3$H]-AV-45. A description of the protocols is provided hereinafter.

[$^3$H]-T808 was obtained by subjecting a solution of the bromo precursor (1 eq.) in methanol to catalytic tritiation over palladium on carbon (5%) in the presence of diisopropylethylamine (5 eq.) at room temperature. The bromo precursor was obtained by bromination of T808 with N-bromosuccinimide (1 eq.) in acetonitrile.

[³H]-AV-45 was obtained by Iridium catalyzed (Crabtree's catalyst) tritium exchange of AV-45 dissolved in dichloromethane.

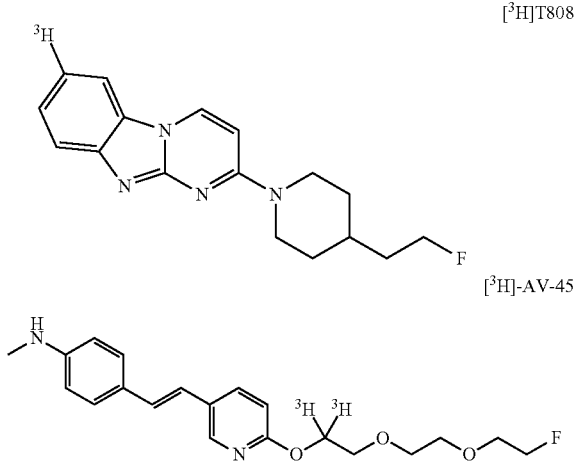

As already mentioned, the compound of Formula (I), in particular the compound of Formula (I'), and compositions comprising the compound of Formula (I), in particular the compound of Formula (I'), can be used for imaging a tissue, or a subject, in vitro or in vivo. In particular, the invention relates to a method of imaging or quantifying tau aggregates in a tissue, or a subject in vitro or in vivo.

In particular, the method of imaging tau aggregates comprises providing a subject, in particular a patient, with a detectable quantity of a compound of Formula (I), in particular a compound of Formula (I').

Further, the invention relates to a method of imaging tau-aggregate deposits comprising the steps of providing a subject with a detectable quantity of a compound of Formula (I), in particular a compound of Formula (I'), allowing sufficient time for the compound of Formula (I), in particular the compound of Formula (I'), to be associated with tau aggregate deposits, and detecting the compound associated with tau aggregate deposits.

When the method is performed in vivo, the compound of Formula (I), in particular the compound of Formula (I'), can be administered intravenously, for example, by injection with a syringe or by means of a peripheral intravenous line, such as a short catheter. The compound of Formula (I), in particular the compound of Formula (I'), or a sterile solution comprising a compound of Formula (I), in particular a compound of Formula (I'), may in particular be administered by intravenous administration in the arm, into any identifiable vein, in particular in the back of the hand, or in the median cubital vein at the elbow.

Thus, in a particular embodiment, the invention relates to a method of imaging a subject, comprising the intravenous administration of a compound of Formula (I), in particular a compound of Formula (I'), as defined herein, or a composition, in particular, a sterile formulation, comprising a compound of Formula (I), in particular a compound of Formula (I'), to the subject, and imaging the subject with a positron-emission tomography imaging system.

In a further embodiment, the invention relates to a method of quantifying tau aggregation deposits in a subject, comprising the intravenous administration of a compound of Formula (I), in particular a compound of Formula (I'), or a composition comprising a compound of Formula (I), in particular a compound of Formula (I'), to the subject, and imaging with a positron-emission tomography imaging system.

The compound is provided to a subject in a detectable quantity and after sufficient time has passed for the compound to become associated with the tau aggregation deposits, the labelled compound is detected noninvasively.

Definitions

As used herein, the term "composition" is intended to encompass a product comprising the specified ingredients in the specified amounts, as well as any product which results, directly or indirectly, from combinations of the specified ingredients in the specified amounts. The term "$C_{1-4}$alkyl" shall denote a straight or branched saturated alkyl group having 1, 2, 3 or 4 carbon atoms, respectively e.g. methyl, ethyl, 1-propyl, 2-propyl, butyl and the like.

Addition salts of the compounds according to the invention also intended to be encompassed within the scope of this invention.

Acceptable salts of the compounds of the invention are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention. The pharmaceutically acceptable salts are defined to comprise the therapeutically active non-toxic acid addition salt forms that the compounds according to the invention are able to form. Said salts can be obtained by treating the base form of the compounds according to the invention with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely, said salt forms can be converted into the free base form by treatment with an appropriate base.

In addition, some of the compounds of the present invention may form solvates with water (i.e., hydrates) or common organic solvents, and such solvates are also intended to be encompassed within the scope of this invention.

The term "subject" as used herein, refers to a human, who is or has been the object of treatment, observation or experiment. Unless otherwise stated, "subject" includes non-symptomatic humans, presymptomatic humans and human patients.

Preparation

The compounds according to the invention can generally be prepared by a succession of steps, each of which is known to the skilled person. In particular, the compounds can be prepared according to the following synthesis methods.

Compounds of Formula [¹⁹F]-(I-a) or [¹⁹F]-(I-b) as disclosed herein can be prepared by a reaction of 6-bromoisoquinoline with an appropriate 2-amino-pyridine compound of Formula (II-a) wherein all variables are as described herein for [¹⁹F]-(I)

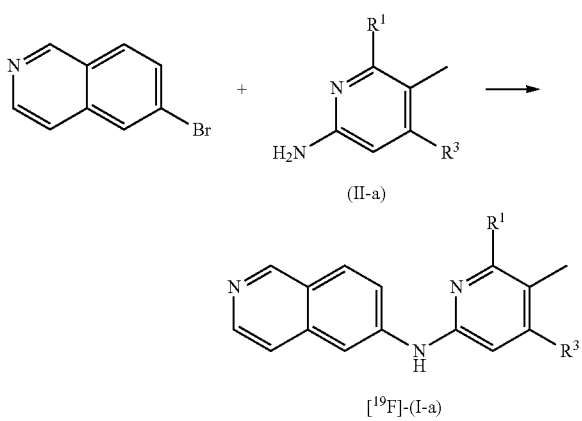

(II-a)

[¹⁹F]-(I-a)

under Buchwald-Hartwig amination conditions, wherein all variables are as described herein for [¹⁹F]-(I), or alternatively, by a reaction of a compound of Formula (II-a') wherein R¹ is —NO₂ and R³ is H, or R is H and R³ is —NO₂, with a fluoride source, such as KF, in a reaction inert solvent, such as DMSO, under thermal conditions,

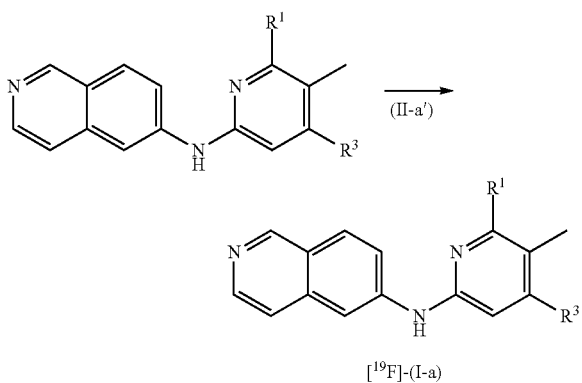

(II-a')

[¹⁹F]-(I-a)

or alternatively, by a reaction of isoquinolin-6-amine with an appropriate 2-chloropyridine compound of Formula (II-b) wherein all variables are as described herein for [¹⁹F]-(I)

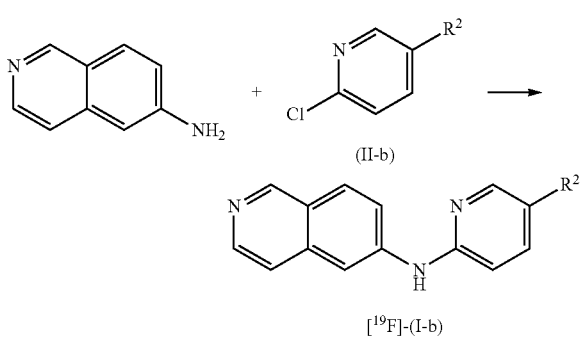

(II-b)

[¹⁹F]-(I-b)

under Buchwald-Hartwig amination conditions.

The compound of Formula (II-a') can be prepared for example, by reaction of isoquinolin-6-amine with 6-bromo-3-methyl-2-nitropyridine or 2-bromo-5-methyl-4-nitropyridine under Buchwald-Hartwig amination conditions.

Applications

The compounds according to the present invention find various applications for imaging tissues, or a subject, both in vitro and in vivo. Thus, for instance, they can be used to map the differential distribution of tau aggregate deposits in subjects of different age and sex. Further, they allow one to explore for differential distribution of tau aggregate deposits in subjects afflicted by different diseases or disorders, including Alzheimer's disease, but also other diseases caused by tau aggregate deposits, i.e. other tauopathies.

Thus, excess distribution may be helpful in diagnosis, case finding, stratification of subject populations, and in monitoring disease progression in individual subjects, particularly when anti-tau treatments, e.g. antibodies, become available. Since the radioligand is administered in trace amounts, i.e. in detectable amounts for PET imaging, no therapeutic effect may be attributed to the administration of the radioligands according to the invention.

Experimental Part

Chemistry

As used herein, the term "ACN or MeCN" means acetonitrile, "aq." means aqueous, "tBuOH" means tert-butanol, "DCM" means dichloromethane, "DIPE" means diisopropyl ether, "DIPEA" means N,N-diisopropylethylamine, "DMF" means N,N-dimethylformamide, "DMSO" means dimethyl sulfoxide, "Et₂O" means diethyl ether, "EtOAc" means ethyl acetate, "h" means hours, "HPLC" means high-performance liquid chromatography. "LCMS" means liquid chromatography/mass spectrometry, "MeOH" means methanol, "min" means minutes, "m.p." means melting point, "org" means organic, "Pd₂(dba)₃" means tris(dibenzylideneacetone)dipalladium(0), "prep" means preparative, "rm/RM" means reaction mixture, "rt/RT" means room temperature", "$R_t$" means retention time (in minutes), "sat." means saturated, "sol." means solution, "TFA" means trifluoroacetic acid, "THF" means tetrahydrofuran, "XantPhos" means 4,5-bis(diphenyl-phosphino)-9,9-dimethylxanthene.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect disposable cartridges purchased from Grace (GraceResolv™ cartridges) or Teledyne ISCO (RediSep® cartridges), on irregular silica gel, particle size 35-70 µm on an ISCO CombiFlash or Biotage Isolera™ Spektra apparatus.

Nuclear Magnetic Resonance (NMR): For a number of compounds, ¹H NMR spectra were recorded either on a Bruker Ultrashield AV300, Bruker DPX 360 MHz NMR or Bruker Avarice III 400 MHz NMR spectrometer with standard pulse sequences, operating at 300 MHz, 360 MHz and 400 MHz, respectively. Samples were dissolved in DMSO-d₆ or CDCl₃ and transferred in 5 mm NMR tubes for the measurement. Chemical shifts (δ) are reported in parts per million (ppm) downfield from tetramethylsilane (TMS), which was used as internal standard.

HPLC purifications were carried out on a GILSON Semi-Preparative System, operated by Trilution software, equipped with a Phenomenex Gemini C18 100A column (100 mm long×30 mm I.D.; 5 µm particles) at RT ° C., with a flow rate of 40 mL/min using a gradient elution in 20 min as indicated in the synthetic protocols. The injection volume was 8000 µL. Acquisition frequency was set to 284 nm for the UV-Dual detector.

Several methods for preparing the compounds of this invention are illustrated in the following examples, which are intended to illustrate but not to limit the scope of the present invention. Unless otherwise noted, all starting materials were obtained from commercial suppliers and used without further purification.

A. Synthesis of Intermediates

Preparation of Intermediate 1

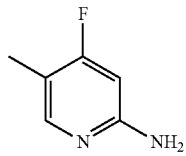

Tetramethyltin (0.736 mL, 5.309 mmol) was added to a mixture of 5-bromo-4-fluoropyridin-2-amine (0.338 g, 1.77 mmol, CAS 944401-69-8), bis(triphenylphosphine)palladium(II) chloride (0.062 g, 0.0885 mmol) and LiCl (0.300 g, 7.078 mmol) in 10 mL DMF. This mixture was sealed in a tube after degassing with nitrogen. Next, the mixture was stirred at 120° C. for 18 hours, after which it was diluted with water. Next, a saturated aqueous solution of KF was added and the aq. layer was extracted with EtOAc. The combined org layers were dried (MgSO$_4$), filtered and the solvents evaporated in vacuo. The crude was purified by flash column chromatography (silica DCM/MeOH, 100/0 to 95/5). The desired fractions were collected and concentrated in vacuo providing intermediate 1 (0.190 g, 79%).

Preparation of Intermediate 2

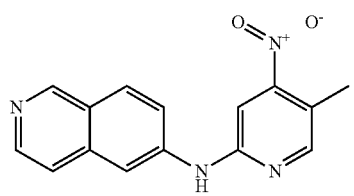

Method 1: To a stirred solution of 6-aminoisoquinoline (18.3 g, 127.1 mmol) in toluene (400 mL) were added 2-bromo-5-methyl-4-nitropyridine (23.0 g, 105.9 mmol), Xantphos (2.45 g, 4.24 mmol), Pd$_2$(dba)$_3$ (1.94 g, 2.12 mmol), tBuOK (16.6 g, 148.3 mmol) under nitrogen. Nitrogen was bubbled through the mixture for 5 min, and then the vial was sealed and heated at 100° C. for 2 h. The mixture was filtered, and the filter cake washed with EtOAc until all product was extracted. Water was added to the filtrate and the org layer was separated, dried (MgSO$_4$), filtered and concentrated. The residue was taken up in water, triturated for 1 h, filtered, and dried in vacuo at 55° C. The resulting brown solid (dissolved in MeOH at pH 4) was purified via Prep HPLC (Stationary phase. RP XBridge Prep C18 OBD-10 μm, 50×150 mm, Mobile phase; 0.55% NH$_4$OAc solution in water+10% CH$_3$CN, MeOH). The pure fractions were combined and the organic component of the eluent was evaporated. A red precipitate formed which was filtered, washed with water and dried. The resulting precipitate was stirred in DCM/MeOH/1 N NaOH (2 L/0.2 L/1 L) until everything dissolved, and the org layer was separated. The aq. layer was extracted once more with DCM. The combined org layers were dried (MgSO$_4$), filtered and evaporated. The residue was triturated in a biphasic mixture of ether and water, filtered and dried in vacuo for 2 days at 50° C., and 4 h in a lyophilizer at rt to give intermediate 2 as orange crystals (6.11 g, 18%). $^1$H NMR (400 MHz, DMSO-d$_6$) δ ppm 2.40 (s, 3H) 7.50 (s, 1H) 7.62-7.71 (m, 2H) 8.01 (d, J=9.0 Hz, 1H) 8.36 (d, J=5.7 Hz, 1H) 8.45 (s, 2H) 9.09 (s, 1H) 9.97 (s, 1H)

Method 2: To a stirred solution of 6-aminoisoquinoline (7.62 g, 52.85 mmol) in 200 mL toluene were added 2-bromo-5-methyl-4-nitropyridine (11.47 g, 52.85 mmol), Xantphos (0.611 g, 1.057 mmol), Pd$_2$(dba)$_3$ (0.484 g, 0.529 mmol) and tBuOK (8.30 g, 74.00 mmol). Nitrogen was bubbled through the mixture for 5 min, and then the vial was sealed and heated at 100° C. for 2 h, and again for 3 h at 110° C. EtOAc was added to the mixture after which it was stirred for 30 min. Next the mixture was filtered over dicalite, and the filter cake washed with EtOAc until all product was extracted. Water was added to the filtrate and the org layer was separated. The aq. layer was extracted with EtOAc until no product remained (LCMS control). The combined org layers were washed with brine, dried (MgSO$_4$), filtered and concentrated. The residue was taken up in water/DIPE, triturated overnight, filtered and dried in vacuo at 55° C. yielding intermediate 2 (10.5 g, 71%, 57% pure), which was used as such for the next reaction step.

Preparation of Intermediate 3

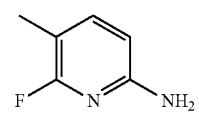

Trimethylboroxine (0.256 mL, 1.83 mmol) was added to a stirred solution of 5-bromo-6-fluoropyridin-2-amine (0.291 g, 1.52 mmol, CAS 944401-65-4), tetrakis(triphenylphosphine)palladium(0) (0.176 g, 0.152 mmol) and Cs$_2$CO$_3$ (0.993 g, 3.047 mmol) in 1,4-dioxane (5.3 mL) while bubbling nitrogen. The reaction was stirred at 105° C. for 16 h under nitrogen. Water and EtOAc were added. The phases were separated and organic was dried over MgSO$_4$, filtered and evaporated. The crude product was purified by flash column chromatography (silica; EtOAc in Heptane, 0/100 to 50/50). The desired fractions were collected and concentrated in vacuo to yield intermediate 3 as a yellow solid (0.151 g, 79%).

Preparation of Intermediate 4

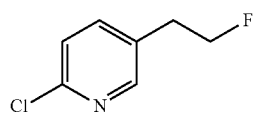

Deoxo-Fluor® (50% m toluene, 1.67 mL, 3.807 mmol) was added dropwise to a solution of 2-chloro-5-(2-fluoroethyl)pyridine (0.400 g, 2.538 mmol, CAS 117528-28-6) in dry DCM (15 mL) at 0° C. After 1 min, the cold bath was removed and reaction mixture was stirred at room temperature for 2 h. The mixture was diluted with aq. sat. NaHCO$_3$ and extracted with DCM. The organic layer was washed with water, dried with (MgSO$_4$), filtered and the solvents evaporated in vacuo. The crude product was purified by flash column chromatography (silica; EtOAc in heptane from 0/100 to 70/30). The desired fractions were collected and concentrated in vacuo yielding intermediate 4 (0.193 g, 45%).

Preparation of Intermediate 5

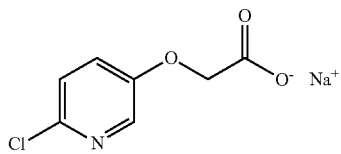 [SMILES: O=C([O-])COc1ccc(Cl)nc1 ; [Na+]]

NaOH (0.064 g, 1.599 mmol) was added to a mixture of [(6-chloropyridin-3-yl)oxy]acetic acid (0.300 g, 1.599 mmol, CAS 234109-28-5) in a mixture of CH$_3$CN (4 mL) and water (4 mL). The mixture was heated at 85° C. for 1 h. The solvent was concentrated in vacuo providing intermediate 5 (335 mg, 95%) as a white solid, which was used as such in the next step.

Preparation of Intermediate 6

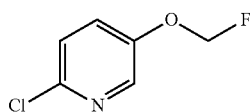

Selectfluor® (1.116 g, 3.15 mmol) was added to a solution of intermediate 5 (0.314 g, 1.5 mmol) in a mixture of water (7.5 mL) and CH$_3$CN (7.5 mL) previously degassed. Tris(2,2'-bipyridyl)dichlororuthenium(II)hexahydrate (0.056 g, 0.075 mmol) was added. The reaction was irradiated by a 500 W visible light shipyard lamp, placed at 30 cm from the reaction, for 1 h. After turning off the light, water and diethylether were poured on the reaction media. The two phases were separated and the aqueous one was extracted with Et$_2$O. The combined organic phases were dried over MgSO$_4$, filtered, and the solvent was evaporated under reduced pressure. The crude was filtered over silica gel with Et$_2$O as eluent and concentrated in vacuo to yield intermediate 6 as a beige oily solid (0.167 g, 54%).

Preparation of Intermediate 7

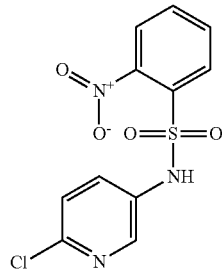 [SMILES: O=[N+]([O-])c1ccccc1S(=O)(=O)Nc1ccc(Cl)nc1]

A stirred solution of 5-amino-2-chloropyridine (1.00 g, 7.778 mmol) in THF (27 mL) was cooled to 0° C., then 2-nitrobenzenesulfonylchloride (1.72 g, 7.778 mmol) and pyridine (0.942 mL, 11.668 mmol) were added to the solution. The resulting mixture was allowed to warm to rt and stirred for 3 hours. 2-Nitrobenzenesulfonylchloride (0.52 g, 2.334 mmol) and pyridine (0.314 mL, 3.889 mmol) were added at 0° C., and the mixture was stirred at rt overnight. Water was then added to the mixture, and the aq. layer was extracted with EtOAc. The extract was washed with saturated aq. NaHCO$_3$ and brine. The org layer was dried over MgSO$_4$, filtered, and evaporated. The residue was purified by flash column chromatography (silica; EtOAc in Heptane, 0/100 to 10/90). The desired fractions were collected and concentrated in vacuo to yield intermediate 7 (2.22 g, 91%).

Preparation of Intermediate 8

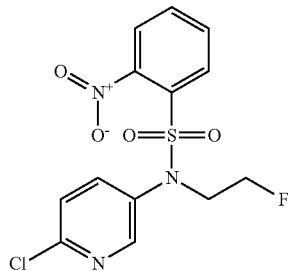 [SMILES: O=[N+]([O-])c1ccccc1S(=O)(=O)N(CCF)c1ccc(Cl)nc1]

Intermediate 7 (1.1 g, 3.506 mmol) and 2-fluoroethyl 4-methylbenzenesulfonate (0.918 g, 4.208 mmol, CAS 383-50-6) were dissolved in DMF (10.6 mL). Cs$_2$CO$_3$ (1.942 g, 5.961 mmol) was added under nitrogen atmosphere. The mixture was heated to 85° C. overnight. After cooling to ambient temperature, the dark brown suspension was diluted with water and extracted with EtOAc. The org layer was washed with brine, dried over MgSO$_4$, filtered and concentrated. The product was purified by flash column chromatography (silica; EtOAc in heptane, 0/100 to 20/80). The desired fractions were collected and concentrated in vacuo providing intermediate 8 (0.687 g, 54%).

Preparation of Intermediate 9

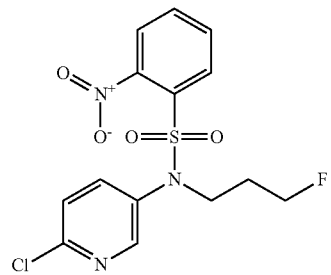 [SMILES: O=[N+]([O-])c1ccccc1S(=O)(=O)N(CCCF)c1ccc(Cl)nc1]

Intermediate 7 (0.700 g 2.231 mmol) and 3-fluoropropyl 4-methylbenzenesulfonate (0.674 g, 2.901 mmol, CAS 312-68-5) were dissolved in DMF (6.7 mL). Cs$_2$CO$_3$ (1.45 g, 4.463 mmol) was added and the mixture was heated to 85° C. overnight under nitrogen atmosphere. 3-Fluoropropyl 4-methylbenzenesulfonate (0.363 g, 1.562 mmol) and Cs$_2$CO$_3$ (0.727 g, 2.231 mmol) were added and the mixture was heated at 85° C. overnight. After cooling to ambient temperature, the dark brown suspension was diluted with water and extracted with EtOAc. The organic layer was washed with brine, dried over MgSO$_4$, filtered and concentrated. The product was purified by flash column chromatography (silica; EtOAc in heptane, 0/100 to 15/85). The desired fractions were collected and concentrated in vacuo yielding intermediate 9 (0.395 g, 42%).

Preparation of Intermediate 10

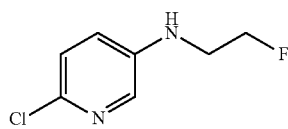 [SMILES: FCCNc1ccc(Cl)nc1]

To a stirred solution of intermediate 8 (0.687 g 1.91 mmol) in 11.6 mL DMF, LiOH·H₂O (0.491 g, 11.46 mmol) and 2-mercaptoethanol (0.164 mL, 2.33 mmol) were added at 0° C. The reaction mixture was stirred at rt for 2 hours. Water was added and the mixture was extracted with EtOAc. The extract was washed with water and dried over MgSO₄. Concentration under reduced pressure gave oily residues. The crude was purified by flash chromatography (silica gel, EtOAc in Heptane, from 0/100 to 30/70). The desired fractions were collected and concentrated in vacuo to yield intermediate 10 as a yellow oil (0.276 g, 83%).

Preparation of Intermediate 11

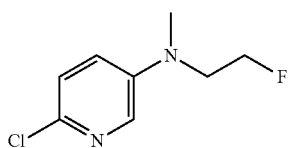

Intermediate 10 (0.200 g, 1.145 mmol) was added to a stirred solution of NaH (60% dispersion in mineral oil, 0.069 g, 1.718 mmol) in DMF (9.2 mL) at 0° C. under a nitrogen atmosphere. After being stirred for 30 min at this temperature, CH₃I (0.134 mL, 1.833 mmol) was added and stirring was continued overnight at rt. NaH (60% dispersion in mineral oil, 0.032 g, 0.802 mmol) was added at 0° C., and the mixture was stirred 30 min. CH₃I (0.032 mL, 0.573 mmol) was added and the mixture was stirred at rt for 2 h. The mixture was diluted with water and extracted with EtOAc. The org layer was dried (MgSO₄), filtered and evaporated in vacuo. The crude product was purified by flash column chromatography (EtOAc in heptane 0/100 to 15/85). The desired fractions were collected and concentrated in vacuo to yield intermediate 11 (0.137 g, 63%).

Preparation of Intermediate 12

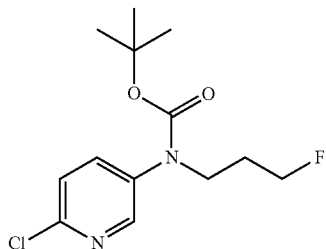 [SMILES: CC(C)(C)OC(=O)N(CCCF)c1ccc(Cl)nc1]

NaH (60% dispersion in mineral oil, 0.178 g, 4.46 mmol) was added to a stirred solution of tert-butyl (6-chloropyridin-3-yl)carbamate (1.36 g, 75% pure, 4.46 mmol, CAS 171178-45-3) in dry DMF (7 mL) at 0° C. under N2. The mixture was stirred at 0° C. for 15 min. Then 1-bromo-3-fluoropropane (0.491 mL, 5.353 mmol) was added at 0° C., and the mixture was allowed to warm to rt and stirred overnight. More 1-bromo-3-fluoropropane (0.327 mL, 3.568 mmol) and NaH (60% dispersion in mineral oil, 0.178 g, 4.46 mmol) were added and the mixture was stirred at rt for 4 h. Additional 1-bromo-3-fluoropropane (0.818 mL, 8.921 mmol) and NaH (600% dispersion in mineral oil, 0.178 g, 4.46 mmol) were added and the mixture was stirred at rt overnight. The reaction mixture was taken up with DCM and washed with a saturated solution of NH₄Cl. The organic layer was separated, dried over MgSO₄, filtered and concentrated in vacuo. The residue was purified by flash column chromatography (silica; EtOAc in heptane 40% to 100%). The desired fractions were recovered and the solvents were evaporated in vacuo to yield intermediate 12 as a colorless oil (1.71 g, 75% pure, quantitative yield).

Preparation of Intermediate 13

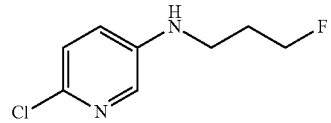 [SMILES: FCCCNc1ccc(Cl)nc1]

Method 1: TFA (4 mL, 53.3 mmol) was added to a mixture of intermediate 12 (1.71 g, 5.33 mmol, 75% pure) in 20 mL DCM at 0° C., and then the mixture was stirred at rt for 150 min. Next, the mixture was diluted with DCM and washed with an aq. sat. sol. of NaHCO₃. The org layer was separated, dried (MgSO₄), filtered and concentrated in vacuo to provide intermediate 13 (1.91 g, 53% pure, quantitative), which was used as such.

Method 2: To a stirred solution of intermediate 7 (0.395 g, 0.93 mmol) in DMF (5.6 mL), LiOH·H₂O (0.239 g, 5.58 mmol) and 2-mercaptoethanol (0.798 mL, 1.134 mmol) were added at 0° C. The reaction mixture was stirred at rt for 2 h, after which it was extracted with EtOAc. The combined org layers were washed with water, dried over MgSO₄ and filtered. Concentration under reduced pressure gave an oily residue which was purified by flash chromatography (silica gel, EtOAc in heptane, from 0/100 to 30170). The desired fractions were collected and concentrated in vacuo to yield intermediate 13 as a yellow oil (0.168 g, 96%).

Preparation of Intermediate 14

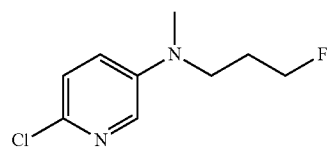

Method 1: Formaldehyde (37% in water, 2.185 mL, 29.162 mmol) was added to a solution of intermediate 13 (obtained from method 1, 1.91 g, 9.721 mmol, 53% pure) in a mixture of acetic acid (0.835 mL) and MeOH (20 mL). Then NaBH₃CN (1.83 g, 29.162 mmol) was added portion wise. The mixture was stirred at rt overnight (15 h). A sat. sol. of NaHCO₃ was added and the mixture was extracted with EtOAc. The org layers were dried over MgSO₄, filtered and concentrated. The crude product was purified by flash column chromatography (silica; EtOAc in heptane, 0/100 to 80/20). The desired fractions were collected and concentrated in vacuo to yield intermediate 14 (0.687 g, 63%) as a colorless oil.

Method 2: Intermediate 13 (obtained from method 2, 0.172 g, 0.912 mmol) was added to a stirred solution of NaH (60% dispersion in mineral oil, 0.055 g, 1.368 mmol) in DMF (7.3 mL) at 0° C. under nitrogen atmosphere. After being stirred for 30 min at this temperature, CH₃I (0.107 mL, 1.459 mmol) was added and stirred overnight at rt. The mixture was diluted with water and extracted with EtOAc. The organic layer was filtered, dried and evaporated in vacuo. The crude product was purified by flash column chromatography (EtOAc in heptane, 0/100 to 10/90). The desired fractions were collected and concentrated in vacuo to yield intermediate 14 (0.143 g, 77%).

Preparation of Intermediate 15

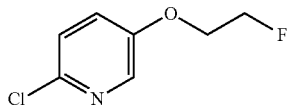 [SMILES: FCCOc1ccc(Cl)nc1]

2-Chloro-5-hydroxypyridine (0.300 g 2.316 mmol) and 2-fluoroethyl-4-methylbenzenesulfonate (0.505 g, 2.316 mmol, CAS 383-50-6) were dissolved in DMF (7 mL). Cs$_2$CO$_3$ (1.132 g, 3.474 mmol) was added under nitrogen atmosphere. The mixture was heated to 85° C. for 5 h. After cooling to ambient temperature, the dark brown suspension was diluted with water and extracted with EtOAc. The org layers were washed with brine, dried over MgSO$_4$, filtered and concentrated. The product was purified by flash column chromatography (silica; EtOAc in heptane 0/100 to 35/65). The desired fractions were collected and concentrated in vacuo providing intermediate 15 (0.374 g, 92%).

Preparation of Intermediate 16

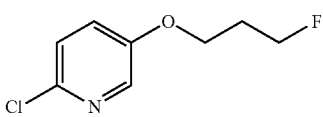 [SMILES: FCCCOc1ccc(Cl)nc1]

2-Chloro-5-hydroxypyridine (0.300 g, 2.316 mmol) and 3-fluoropropyl 4-methylbenzenesulfonate (0.538 g, 2.316 mmol, CAS 312-68-5) were dissolved in DMF (7 mL). Cs$_2$CO$_3$ (1.132 g, 3.474 mmol) was added under nitrogen atmosphere. The mixture was heated to 85° C. for 5 h. After cooling to ambient temperature, the dark brown suspension was diluted with water and extracted with EtOAc. The organic layer was washed with brine, dried over MgSO$_4$, filtered and concentrated. The product was purified by flash column chromatography (silica; EtOAc in heptane, 0/100 to 30/70). The desired fractions were collected and concentrated in vacuo providing intermediate 16 (0.408 g, 93%).

Preparation of Intermediate 17

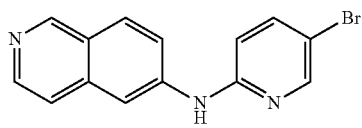 [SMILES: Brc1ccc(Nc2ccc3cnccc3c2)nc1]

K$_3$PO$_4$ (1.70 g, 7.99 mmol), Pd$_2$(dba)$_3$ (0.152 g, 0.166 mmol) and Xantphos (0.161 mg, 0.277 mmol) were added to a solution of 2,5-dibromopyridine (0.738 g, 3.052 mmol, CAS 624-28-2) in dry THF (20 mL) while nitrogen was bubbling through the mixture. After 10 min, 6-aminoisoquinoline (0.400 g, 2.774 mmol, CAS 23687-26-5) was added and the mixture was stirred at rt for 10 min. Then, the mixture was heated at 100° C. for 16 h. After cooling to rt, the mixture was washed with aq. sat. NaHCO$_3$ and extracted with EtOAc. The organic layer was dried over MgSO$_4$, filtered and the solvent was evaporated in vacuo. The crude product was purified by flash column chromatography (silica; EtOAc in heptane 0/100 to 75/25). The desired fractions were collected and concentrated in vacuo providing intermediate 17 (0.680 g, 80% pure, 65% yield).

Preparation of Intermediate 18

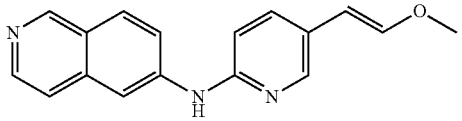 [SMILES: CO/C=C/c1ccc(Nc2ccc3cnccc3c2)nc1]

Mixture of E (Major) and Z (Minor) Isomer

Intermediate 17 (0.680 g, 1.812 mmol) in 1,4-dioxane (10.2 mL) was degassed for 10 min. 2-[2-Ethoxy vinyl]-4,4,5,5-tetramethyl-1,3,2-dioxaborolane (0.538 g, 2.719 mmol, CAS 1201905-61-4, prepared according to procedure described in WO2012010538, 2:1 mixture of E and Z), Pd(OAc)$_2$ (0.020 g 0.0906 mmol), X-Phos (0.095 g, 0.199 mmol) and Cs$_2$CO$_3$ (0.886 g, 2.719 mmol) were added followed by degassed water (1.1 mL). The mixture was degassed for another 10 min and was stirred at 80° C. for 6 h. The mixture was then cooled to ambient temperature and diluted with EtOAc. The org phase was washed with water and brine, dried over MgSO$_4$, filtered and concentrated. The crude product was purified by flash column chromatography (silica; EtOAc in heptane 0/100 to 100/0). The desired fractions were collected and concentrated in vacuo providing intermediate 18 (0.510 g, 91%, mixture of E and Z).

Preparation of Intermediate 19

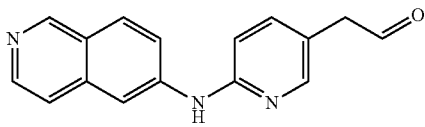 [SMILES: O=CCc1ccc(Nc2ccc3cnccc3c2)nc1]

To a mixture of intermediate 18 (0.510 g, 1.75 mmol) in THF (5.3 mL) was added HCl (2 M in water, 3.939 mL, 7.877 mmol). The mixture was stirred at 60° C. overnight. NaHCO$_3$ sat. was added until pH 7. The mixture was extracted with EtOAc. The org layer was separated, dried (MgSO$_4$), filtered and the solvents were evaporated in vacuo providing intermediate 19. The product was used as such in the next step (0.378 g, 82%).

Preparation of Intermediate 20

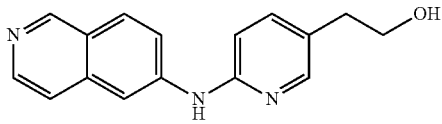 [SMILES: OCCc1ccc(Nc2ccc3cnccc3c2)nc1]

NaBH$_4$ (0.054 g, 1.436 mmol) was added to a solution of intermediate 19 in MeOH (4.5 mL) at 0° C. The mixture was stirred at rt for 30 min. Water was added and the mixture was extracted with EtOAc. The org layer was separated, dried (MgSO$_4$), filtered and the solvents were evaporated in vacuo. The crude product was purified by flash column chromatography (silica; MeOH in DCM 0/100 to 10/90). The desired fractions were collected and concentrated in vacuo providing intermediate 20 (0.135 g, 35%).

B. Preparation of Compounds of Formula [¹⁹F](I)

Preparation of Compound 1

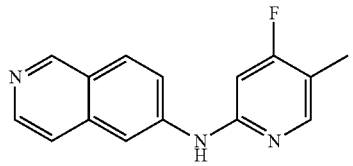 [SMILES: Cc1cnc(Nc2ccc3cnccc3c2)cc1F]

Method 1: K₃PO₄ (0.872 g, 4.11 mmol), Pd₂(dba)₃ (0.078 g, 0.0856 mmol) and Xantphos (0.083 g, 0.143 mmol) were added to a solution of 6-bromoisoquinoline (0.327 g, 1.57 mmol) in dry DMF (15 mL) while nitrogen was bubbled through the mixture. After 10 min, intermediate 1 (0.180 g, 1.427 mmol) was added and the mixture was stirred at rt for 10 min. Then, the mixture was heated at 100° C. for 16 h. After cooling to rt, the mixture was washed with sat. NaHCO₃ and extracted with EtOAc. The org layer was dried over MgSO₄, filtered and the solvent was evaporated in vacuo. The crude product was purified by flash column chromatography (silica; DCM/MeOH, from 100/0 to 95/5). The desired fractions were collected and concentrated in vacuo. The product was further purified by reverse phase from 70% H₂O (25 mM NH₄HCO₃)-30% MeCN-MeOH to 27% H₂O (25 mM NH₄HCO₃)-73% MeCN-MeOH. The desired fractions were collected and concentrated in vacuo. The product was triturated with DIPE to yield compound 1 as a white solid (0.150 g, 41%).

Method 2: KF (10.2 g, 175.7 mmol) was added to intermediate 2 (obtained from method 2, 9.85 g, 35.14 mmol) in DMSO (236 mL). The resulting mixture was stirred for 16 h at 160° C., after which LCMS showed full conversion. Water and DCM were added, the biphasic mixture was shaken, and then filtered over Dicalite®. The org. layer was separated and the aq. layer extracted with DCM. The combined org layers were dried (MgSO₄), filtered and evaporated to dryness. The red-brown residue was purified by flash column chromatography over 120 g silica gel using a gradient (heptane/EtOAc, 1:0 to 0:1). The product fractions were evaporated to dryness providing a brown solid. A purification was performed via Prep HPLC (Stationary phase: RP XBridge Prep C18 OBD-10 µm, 50×150 mm, Mobile phase: 0.25% NH₄HCO₃ solution in water, MeOH) yielding compound 1 as white crystals (1.38 g, 15.5%) after evaporation of the eluent, suspending in water, filtering, washing with heptane, and drying in vacuo. ¹H NMR (400 MHz, DMSO-d₆) δ ppm 2.17 (s, 3H) 6.75 (d, J=11.9 Hz, 1H) 7.62 (d, J=5.7 Hz, 1H) 7.66 (dd, J=8.9, 2.1 Hz, 1H) 7.97 (d, J=8.8 Hz, 1H) 8.20 (d, J=11.2 Hz, 1H) 8.33 (d, J=5.7 Hz, 1H) 8.42 (d, J=1.8 Hz, 1H) 9.06 (s, 1H) 9.61 (s, 1H)

Preparation of Compound 2

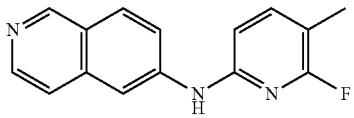 [SMILES: Cc1ccc(Nc2ccc3cnccc3c2)nc1F]

K₃PO₄ (0.462 g, 2.175 mmol), Pd₂(dba)₃ (0.041 g, 0.0453 mmol) and Xantphos (0.044 g, 0.0755 mmol) were added to a solution of intermediate 3 (0.100 g, 0.793 mmol) in dry THF while nitrogen was bubbling through the mixture. After 10 min, 6-bromoisoquinoline (0.157 g, 0.755 mmol) was added and the mixture was stirred at rt for 10 min. Then, the mixture was heated at 100° C. for 16 h. After cooling to rt, the mixture was washed with aq. sat. NaHCO₃ and extracted with EtOAc. The organic layer was dried over MgSO₄, filtered and the solvent was evaporated in vacuo. The crude product was purified by flash column chromatography (silica; DCM/MeOH, 100/0 to 95/5). The desired fractions were collected and concentrated in vacuo. The residue was purified by preparative HPLC ((0.1% HCOOH)/25 mM NH₄HCO₃); from 70/30 to 27/73). The desired fractions were collected and concentrated in vacuo yielding compound 2 (0.0238 g, 12%) ¹H NMR (300 MHz, CHLOROFORM-d) δ ppm 2.24 (s, 3H) 6.72-6.86 (m, 2H) 7.40-7.60 (m, 3H) 7.89 (d, J=8.7 Hz, 1H) 7.93 (br s, 1H) 8.44 (d, J=5.8 Hz, 1H) 9.10 (br s, 1H)

Preparation of Compound 3

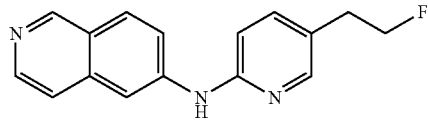 [SMILES: FCCc1ccc(Nc2ccc3cnccc3c2)nc1]

K₃PO₄ (0.300 g, 1.415 mmol), Pd₂(dba)₃ (0.027 g, 0.0295 mmol) and Xantphos (0.028 g, 0.0491 mmol) were added to a solution of intermediate 4 (0.080 g, 0.491 mmol) in dry THF (5 mL) while nitrogen was bubbling through the mixture. After 10 min, isoquinolin-6-amine (0.074 g, 0.516 mmol, CAS 23687-26-5) was added and the mixture was stirred at rt for 10 min. Then, the mixture was heated at 90° C. for 16 h. After cooling to rt, the mixture was washed with sat. NaHCO₃ and extracted with EtOAc. The org layer was dried over MgSO₄, filtered and the solvent was evaporated in vacuo. The crude product was purified by flash column chromatography (silica; MeOH in DCM, 0/100 to 3/97). The desired fractions were collected and concentrated in vacuo. The product was further purified by preparative HPLC ((0.1% HCOOH)/ACN:MeOH 1:1); from 95/5 to 63/37). The desired fractions were collected, concentrated in vacuo to yield compound 3 (0.051 g, 38%). ¹H NMR (300 MHz, CHLOROFORM-d) δ ppm 2.98 (dt, J=24.7, 6.2 Hz, 2H) 4.64 (dt, J=47.0, 6.3 Hz, 2H) 6.82 (br s, 1H) 6.98 (d, J=8.4 Hz, 1H) 7.43-7.56 (m, 3H) 7.89 (d, J=8.8 Hz, 1H) 7.98 (s, 1H) 8.22 (s, 1H) 8.43 (d, J=5.8 Hz, 1H) 9.10 (s, 1H).

Compound 3 can be also made alternatively from intermediate 20, for example, by formation of the corresponding methanesulfonate or 4-toluenesulfonate followed by displacement with a source of fluoride.

Preparation of Compound 4

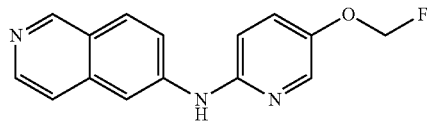 [SMILES: FCOc1ccc(Nc2ccc3cnccc3c2)nc1]

K₃PO₄ (0.481 g, 2.264 mmol), Pd₂(dba)₃ (0.043 g, 0.0472 mmol) and Xantphos (0.045 g, 0.0786 mmol) were added to a solution of intermediate 6 (0.127 g, 0.786 mmol) in THF (6 mL) while nitrogen was bubbling. After 10 min, isoquinolin-6-amine (0.125 g, 0.865 mmol, CAS 23687-26-5) was added and the mixture was stirred at rt for 10 min. Then, the mixture was heated at 90° C. for 16 h. After cooling to rt, the mixture was washed with sat. NaHCO₃ and extracted with EtOAc. The organic layer was dried over MgSO₄, filtered and the solvent was evaporated in vacuo. The crude product was purified by flash column chromatography (silica: EtOAc in heptane from 5/95 to 100/0). The desired fractions were collected and concentrated in vacuo. The product was purified by preparative HPLC ((from 59% H₂O (25 mM NH₄HCO₃)-41% MeCN-MeOH to 17% H₂O (25 mM NH₄HCO₃)-83% MeCN-MeOH). The desired fractions were collected and concentrated in vacuo. The product was triturated with n-pentane to yield compound 4 as a beige solid (0.075 g, 34%). ¹H NMR (300 MHz, CHLOROFORM-d) δ ppm 5.69 (d, J=54.6 Hz, 2H) 6.80 (br s, 1H) 7.00 (d, J=8.9 Hz, 1H) 7.39-7.47 (m, 1H) 7.54 (d, J=5.8 Hz, 1H) 7.89 (d, J=8.8 Hz, 1H) 7.97 (s, 1H) 8.22 (d, J=2.1 Hz, 1H) 8.43 (d, J=5.8 Hz, 1H) 9.09 (s, 1H)

Preparation of Compound 5

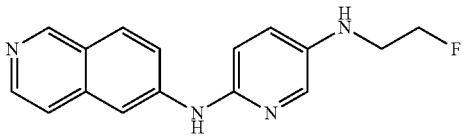 [SMILES: FCCNc1ccc(Nc2ccc3cnccc3c2)nc1]

K₃PO₄ (0.294 g, 1.386 mmol), Pd₂(dba)₃ (0.026 g, 0.0289 mmol) and Xantphos (0.028 g, 0.0481 mmol) were added to a solution of intermediate 10 (0.084 g, 0.481 mmol) in THF (4 mL) while nitrogen was bubbling. After 10 min, isoquinolin-6-amine (0.069 g 0.481 mmol) was added and the mixture was stirred at rt for 10 min. Then, the mixture was heated at 100° C. for 16 h. Pd₂(dba)₃ (0.026 g, 0.0289 mmol) and Xantphos (0.028 g, 0.0481 mmol) were added while nitrogen was bubbling, and the mixture was further heated at 100° C. overnight. Pd₂(dba)₃ (0.026 g, 0.0289 mmol) and Xantphos (0.028 g, 0.0481 mmol) were added while nitrogen was bubbling, and the mixture was further heated at 100° C. overnight. The mixture was washed with aq. sat. NaHCO₃ and extracted with EtOAc. The organic layer was dried over MgSO₄, filtered and the solvent was evaporated in vacuo. The crude product was purified by flash column chromatography (silica; EtOAc in DCM 0/100 to 50/50). The desired fractions were collected and concentrated in vacuo. The product was further purified by preparative HPLC (from 75% [25 mM NH₄HCO₃]-25% [ACN: MeOH 1:1] to 38% [25 mM NH₄HCO₃]-62% [ACN: MeOH 1:1]). The desired fractions were collected and the solvent was evaporated. The product was triturated with Et₂O and filtrated to yield compound 5 (0.042 g, 31%). ¹H NMR (300 MHz, DMSO-d₆) δ ppm 3.34-3.48 (m, 2H) 4.58 (dt, J=47.6, 4.8 Hz, 2H) 5.63 (br t, J=5.9 Hz, 1H) 6.86 (d, J=8.8 Hz, 1H) 7.11 (dd, J=8.8, 2.7 Hz, 1H) 7.47-7.57 (m, 2H) 7.78 (d, J=2.5 Hz, 1H) 7.87 (d, J=8.9 Hz, 1H) 8.21-8.31 (m, 2H) 8.96 (s, 1H) 9.12 (s, 1H)

Preparation of Compound 6

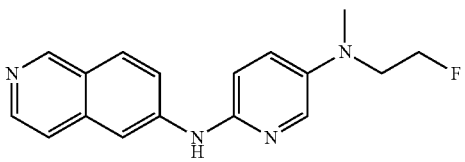 [SMILES: CN(CCF)c1ccc(Nc2ccc3cnccc3c2)nc1]

K₃PO₄ (0.444 g, 2.092 mmol), Pd₂(dba)₃ (0.040 g, 0.0436 mmol) and Xantphos (0.042 g, 0.0726 mmol) were added to a solution of intermediate 11 (0.137 g, 0.726 mmol) in THF (6 mL) while nitrogen was bubbling. After 10 min, isoquinolin-6-amine (0.105 g, 0.726 mmol) was added and the mixture was stirred at rt for 10 min. Then, the mixture was heated at 100° C. for 16 h. More Pd₂(dba)₃ (0.026 g, 0.0289 mmol) and Xantphos (0.028 g, 0.0481 mmol) were added while nitrogen was bubbling through the mixture, after which it was further heated at 100° C. overnight. The mixture was washed with aq. sat. NaHCO₃ and extracted with EtOAc. The combined organic layers were dried over MgSO₄, filtered and the solvent was evaporated in vacuo. The crude product was purified by flash column chromatography (silica: EtOAc in DCM 0/100 to 65/35). The desired fractions were collected and concentrated in vacuo. The product was further purified by preparative HPLC (from 70% [25 mM NH₄HCO₃]-30% [ACN: MeOH 1:1] to 27% [25 mM NH₄HCO₃]-73% [ACN: MeOH 1:1]). The desired fractions were collected and the solvent was evaporated. The product was triturated with Et₂O and filtrated to yield compound 6 (0.092 g, 43%). ¹H NMR (300 MHz. DMSO-d₆) S ppm 2.93 (s, 3H) 3.62 (dt, J=26.7, 4.6 Hz, 2H) 4.60 (dt, J=47.7, 4.7 Hz, 2H) 6.93 (d, J=9.1 Hz, 1H) 7.28 (dd, J=9.0, 2.7 Hz, 1H) 7.46-7.60 (m, 2H) 7.82-7.94 (m, 2H) 8.27 (d, J=5.8 Hz, 1H) 8.34 (s, 1H) 8.97 (s, 1H) 9.21 (s, 1H)

Preparation of Compound 7

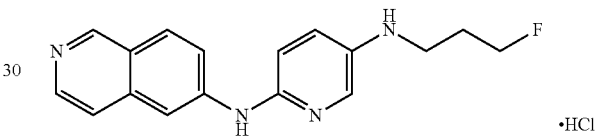

K₃PO₄ (0.544 g, 2.565 mmol), Pd₂(dba)₃ (0.049 g, 0.0534 mmol) and Xantphos (0.052 g, 0.0891 mmol) were added to a solution of intermediate 13 (0.168 g, 0.891 mmol) in THF (6 mL) while nitrogen was bubbling. After 10 min, isoquinolin-6-amine (0.128 g, 0.891 mmol) was added and the mixture was stirred at rt for 10 min. Then, the mixture was heated at 100° C. for 16 h. More Pd₂(dba)₃ (0.049 g, 0.0534 mmol) and Xantphos (0.052 g, 0.0891 mmol) were added under nitrogen flow, and the mixture was heated again at 100° C. overnight. Pd₂(dba)₃ (0.049 g, 0.0534 mmol) and Xantphos (0.052 g, 0.0891 mmol) were added were added under nitrogen flow, and the mixture was heated again at 100° C. for 6 h. The mixture was washed with sat. NaHCO₃ and extracted with EtOAc. The org layers were dried over MgSO₄, filtered and the solvent was evaporated in vacuo. The crude product was purified by flash column chromatography (silica EtOAc in DCM 0/100 to 45/55). The desired fractions were collected and concentrated in vacuo. The product was purified by preparative HPLC (from 75% [25 mM NH₄HCO₃]-25% [ACN: MeOH 1:1] to 0% [25 mM NH₄HCO₃]-100% [ACN: MeOH 1:1]). The desired fractions were collected and the solvent was evaporated. The residue was dissolved in DCM and HCl (5 M in 2-propanol) was added and the resulting mixture was concentrated in vacuo. The residue was triturated with Et₂O and filtered to yield compound 7 as an orange solid (0.066 g, 22% yield). ¹H NMR (300 MHz, DMSO-d₆) δ ppm 1.83-2.05 (m, 2H) 3.17 (br t, J=6.8 Hz, 2H) 4.58 (dt, J=47.4, 5.8 Hz, 2H) 5.83 (br s, 1H) 7.00 (d, J=8.8 Hz, 1H) 7.12 (dd, J=8.7, 2.7 Hz, 1H) 7.77 (dd, J=9.2, 1.2 Hz, 1H) 7.81 (d, J=2.5 Hz, 1H) 7.99 (d, J=6.9 Hz, 1H) 8.20 (d, J=9.1 Hz, 1H) 8.28 (d, J=6.6 Hz, 1H) 8.42 (s, 1H) 9.30 (s, 1H) 10.08 (s, 1H)

Preparation of Compound 8

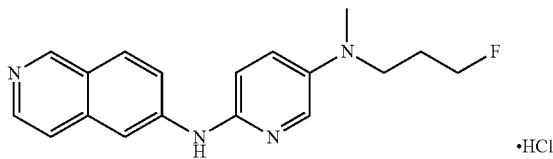 [SMILES: CN(CCCF)c1ccc(Nc2ccc3cnccc3c2)nc1 ; Cl]

K$_3$PO$_4$ (0.431 g, 2.032 mmol), Pd$_2$(dba)$_3$ (0.039 g, 0.0423 mmol) and Xantphos (0.041 g, 0.0706 mmol) were added to a solution of intermediate 14 (0.143 g, 0.706 mmol) in THF (5.9 mL) while nitrogen was bubbling through the mixture. After 10 min, isoquinolin-6-amine (0.102 g, 0.706 mmol) was added and the mixture was stirred at rt for 10 min. Then, the mixture was heated at 100° C. for 16 h. Additional Pd$_2$(dba)$_3$ (0.039 g, 0.0423 mmol) and Xantphos (0.041 g, 0.0706 mmol) were added while nitrogen was bubbling through the mixture, after which it was heated at 100° C. overnight. Additional Pd$_2$(dba)$_3$ (0.039 g, 0.0423 mmol) and Xantphos (0.041 g, 0.0706 mmol) were added while nitrogen was bubbling, and the mixture was heated at 100° C. for 6 h. The mixture was washed with sat. NaHCO$_3$ and extracted with EtOAc. The org layer was dried over MgSO$_4$, filtered and the solvent was evaporated in vacuo. The crude product was purified by flash column chromatography (silica; EtOAc in DCM 0/100 to 20/80). The desired fractions were collected and concentrated in vacuo. The product was further purified by preparative HPLC (from 75% [25 mM NH$_4$HCO$_3$]-25% [ACN: MeOH 1:1] to 0% [25 mM NH$_4$HCO$_3$]-100% [ACN: MeOH 1:1]). The desired fractions were collected and the solvent was evaporated. The crude was dissolved in DCM, HCl (5 N in 2-propanol) was added and the mixture was concentrated in vacuo. The residue was triturated with Et$_2$O and filtered to yield compound 8 as an orange solid (0.058 g, 23%). $^1$H NMR (300 MHz, DMSO-d$_6$) δ ppm 1.78-2.02 (m, 2H) 2.92 (s, 3H) 3.45 (br t, J=7.1 Hz, 2H) 4.52 (dt, J=47.4, 5.7 Hz, 2H) 7.09 (d, J=8.9 Hz, 1H) 7.29 (dd, J=9.0, 3.0 Hz, 1H) 7.81 (dd, J=8.8, 1.2 Hz, 1H) 7.91 (d, J=2.6 Hz, 1H) 7.98 (d, J=6.6 Hz, 1H) 8.21 (d, J=9.1 Hz, 1H) 8.29 (d, J=6.7 Hz, 1H) 8.51 (s, 1H) 9.32 (s, 1H) 10.20 (s, 1H)

Preparation of Compound 9

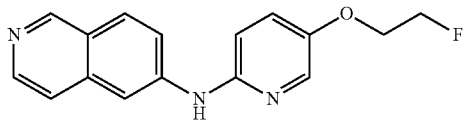 [SMILES: FCCOc1ccc(Nc2ccc3cnccc3c2)nc1]

K$_3$PO$_4$ (0.449 g, 2.117 mmol), Pd$_2$(dba)$_3$ (0.040 g, 0.0441 mmol) and Xantphos (0.043 g, 0.0735 mmol) were added to a solution of intermediate 15 (0.142 g, 0.809 mmol) in THF (4 mL) while nitrogen was bubbling through the mixture. After 10 min, isoquinolin-6-amine (0.106 g, 0.735 mmol) was added and the mixture was stirred at rt for 10 min. Then, the mixture was heated at 100° C. for 16 h. After cooling to rt, the mixture was washed with aq. sat. NaHCO$_3$ and extracted with EtOAc. The combined organic layers were dried over MgSO$_4$, filtered and the solvent was evaporated in vacuo. The crude product was purified by flash column chromatography (silica gel; EtOAc in Heptane, 0/100 to 40/60). The desired fractions were collected and concentrated in vacuo. The product was triturated with di-isopropyl ether and filtered to yield compound 9 as a beige solid (0.116 g, 55%). $^1$H NMR (300 MHz, DMSO-d$_6$) δ ppm 4.28 (br dt, J=30.2, 3.3 Hz, 2H) 4.75 (br dt, J=47.9, 3.3 Hz, 2H) 6.99 (d, J=8.9 Hz, 1H) 7.43 (dd, J=8.9, 2.7 Hz, 1H) 7.52-7.68 (m, 2H) 7.93 (d, J=8.8 Hz, 1H) 8.07 (d, J=2.5 Hz, 1H) 8.30 (br d, J=5.6 Hz, 1H) 8.42 (s, 1H) 9.02 (s, 1H) 9.44 (s, 1H)

Preparation of Compound 10

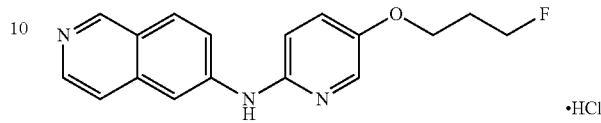

K$_3$PO$_4$ (0.449 g, 2.117 mmol), Pd$_2$(dba)$_3$ (0.040 g 0.0441 mmol) and Xantphos (0.043 g, 0.0735 mmol) were added to a solution of intermediate 16 (0.153 g, 0.809 mmol) in THF (4 mL) while nitrogen was bubbling through the mixture. After 10 min, isoquinolin-6-amine (0.106 g, 0.735 mmol) was added and the mixture was stirred at rt for 10 min. Then, the mixture was heated at 100° C. for 16 h. The mixture was washed with aq. sat. NaHCO$_3$ and extracted with EtOAc. The combined org layers were dried over MgSO$_4$, filtered and the solvent was evaporated in vacuo. The crude product was purified by flash column chromatography, (silica; EtOAc in Heptane, 0/100 to 35/65). The desired fractions were collected and concentrated in vacuo. The residue was dissolved in DCM, HCl (5 N in 2-propanol) was added and the mixture was concentrated in vacuo. The residue was triturated with DIPE and filtered to yield compound 10 as a yellow solid (0.147 g, 47%). $^1$H NMR (300 MHz, DMSO-d$_6$) δ ppm 2.00-2.23 (m, 2H) 4.16 (t, J=6.2 Hz, 2H) 4.63 (dt, J=47.3, 5.8 Hz, 2H) 7.18 (d, J=8.9 Hz, 1H) 7.51 (dd, J=8.9, 3.0 Hz, 1H) 7.91 (dd, J=9.2, 1.4 Hz, 1H) 8.07 (d, J=6.7 Hz, 1H) 8.13 (d, J=2.7 Hz, 1H) 8.28 (d, J=9.1 Hz, 1H) 8.34 (d, J=6.6 Hz, 1H) 8.63 (s, 1H) 9.41 (s, 1H) 10.44 (s, 1H)

C. Radiosynthesis

Materials and Methods

General

The nonradioactive reference material for T808 was synthesized by Janssen Research & Development (a division of Janssen Pharmaceutica NV, Beerse, Belgium) following literature reports (Declercq L., Celen S., Lecina J. et al. *Molecular Imaging* 2016, 15, 1-151). All chemicals and reagents were purchased from commercial sources and used without further purification. HPLC analysis was performed on a LaChrom Elite HPLC system (Hitachi, Darmstadt, Germany) connected to a UV detector set at 254 nm. For analysis of radiolabeled compounds, the HPLC eluate, after passing through the UV-detector, was led over a 3-inch NaI (Tl) scintillation detector connected to a single channel analyzer (GABI box; Raytest, Straubenhardt, Germany). Data were acquired and analyzed using GINA Star (Raytest) data acquisition systems.

Tritiation Co. No. 1

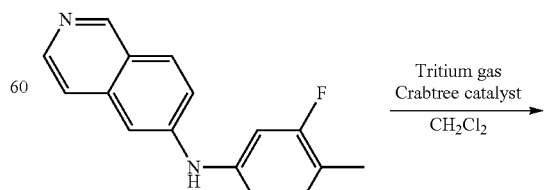

Co. No. 1

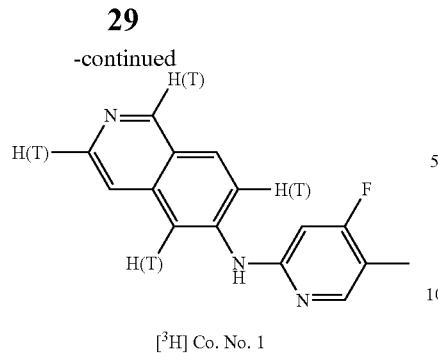

[³H] Co. No. 1

Co. No. 1 (1.74 mg, 6.87 μmol) and (1,2,5,6-η)-1,5-cyclooctadiene](pyridine) (tricyclohexylphosphine)iridium (I) hexafluorophosphate, also referred to as Crabtree's catalyst (7.72 mg, 9.59 μmol) was dissolved in CH₂Cl₂ (0.6 mL). The bright orange solution was degassed three times on an RC Tritec tritiation manifold and then stirred under an atmosphere of tritium gas (8.9 Ci) for 3.5 h at room temperature. The maximum pressure reached during the reaction was 882 mbar. After reaction, the solvent was removed under vacuo. Labile tritium was exchanged by adding methanol (0.8 mL), stirring the solution, and removing the solvent again under vacuo. This process was repeated three times to afford a dried solid crude product.

The crude product was purified by HPLC method: Macherey+Nagel Nucleodur Gravity C18, 5 μm, 8×150 mm column; mobile phase A: water with 0.1% TFA. B: acetonitrile with 0.1% TFA; isocratic at 27% B: flow rate 3.1 mL/min, 230 nm and 254 nm, 20° C. After HPLC, the pH of the collected product fractions was set to neutral with an aqueous solution of NaHCO₃ (10%). The volume of the mixture was reduced on a rotary evaporator. Then the product was extracted with a Phenomenex StrataX cartridge (3 mL, 100 mg), which was eluted with ethanol (5 mL). The product received was further purified by HPLC under basic conditions: Macherey+Nagel Nucleodur Sphinx RP, 5 μm, 8×150 mm; mobile phase A: 10 mM NH₄OAc with 0.05% NH₄OH, B: acetonitrile; isocratic at 46.5% B: flow rate 3.1 mL/min, 230 nm and 254 nm, 20° C. The volume of the collected product fractions was reduced on a rotary evaporator. Then the product was extracted with a Phenomenex StrataX cartridge (3 mL, 100 mg), which was eluted with ethanol (5 mL).

The radiochemical purity of PHI Co. No. 1 was determined to be >99% by the following HPLC method: Column: Macherey+Nagel Nucleodur Sphinx RP (5 μm), 4.6×150 mm, Column temperature: 30° C., Mobile phase A: 10 mM NH₄OAc with 0.05% v/v NH₄OH in water, Mobile phase B: Acetonitrile, Flow rate: 1.0 mL/min, Injection volume: 5 μL, Detection wavelength: UV at 254 nm, Elution gradient: Gradient from 5% B to 95% B in 0-20 min; isocratic at 95% B in 20-25 min: gradient from 95% B to 5% B in 25-25.5 min. The radioactivity flow detector was a Berthold LB 513 with Zinsser Quickszint Flow 302 cocktail at a flow rate of 3.0 mL/min.

The specific activity was determined to 57.7 mCi/mmol by mass spectrometry. LCMS conditions: Agilent Zorbax SB C18 (1.8 μm) 2.1×50 mm column: Mobile phase A: water 0.1% formic acid, B: MeCN 0.1% formic acid: 0 min 5% B; 0.2 min 5% B; 5 min 80% B; Flow rate 0.6 mL/min: Injection 1.0 μL (1.06 μCi, 39.2 KBq), UV-detection 225 nm: Temperature 60° C.

Radiofluorination Co. No. 1 (N=6)

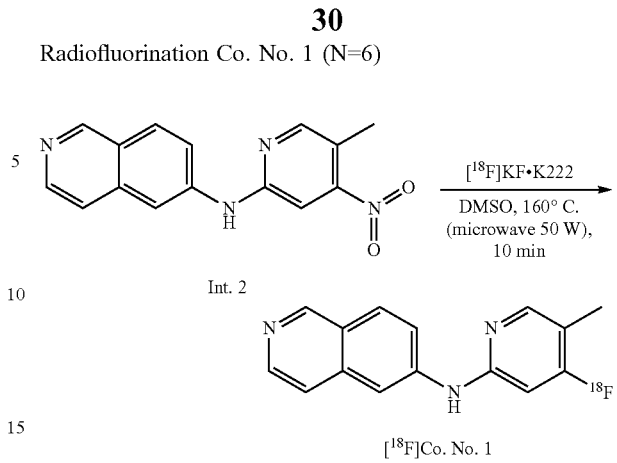

[¹⁸F]Co. No. 1

Fluoride-18 ([¹⁸F]F⁻) was produced by an ¹⁸O(p,n)¹⁸F nuclear reaction in a Cyclone 18/9 cyclotron (Ion Beam Applications, Louvain-la-Neuve, Belgium) by irradiation of 2 mL of 97% enriched ¹⁸O—H₂O (Rotem HYOX18, Rotem Industries, Beer Sheva, Israel) with 18-MeV protons. After irradiation, [¹⁸F]F⁻ was trapped on a SepPak Light Accell plus QMA anion exchange cartridge (CO₃²⁻ form, Waters, Milford, MA, U.S.A.) and eluted with a mixture of Kryptofix 2.2.2 (K-222, 27.86 mg) and K₂CO₃ (2.46 mg) dissolved in CH₃CN/H₂O (0.75 mL; 95:5 v/v). After evaporation of the solvent with a stream of helium at 80° C., and 35 W (microwave cavity), anhydrous CH₃CN (1 mL) was added, and [¹⁸F]F⁻ was further dried under the same conditions. A solution of 0.50 mg of the nitro precursor in 0.25 mL DMSO was added to the dried [¹⁸F]F⁻/K₂CO₃/K-222 residue and the mixture was heated at 160° C., and 50 W for 10 min in a microwave cavity. The crude radiolabelling mixture was diluted with 0.6 mL preparative buffer (0.01 M Na₂HPO₄ pH 7.4 and EtOH (60:40 v/v)) and purified using reverse phase HPLC (RP-HPLC) on an XBridge C18 column (5 μm, 4.6 mm×150 mm; Waters, Milford, U.S.A.) eluted with a mixture of Na₂HPO₄ pH 7.4 and EtOH (60:40 v/v) at a flow rate of 0.8 mL/min and with UV detection at 254 nm. [¹⁸F]Co. No. 1 eluted at 27 min. The purified radiotracer solution was diluted with saline to obtain an ethanol concentration <10%, suitable for intravenous injection. The solution was subsequently passed through a 0.22-μm filter (Millex-GV, Millipore, Billerica, MA, U.S.A.) to obtain a sterile product. Quality control was performed using RP-HPLC on an XBridge column (C₁₈, 3.5 μm, 3.0 mm×100 mm; Waters, Milford, U.S.A.) eluted with a mixture of 0.01 M Na₂HPO₄ pH 7.4 and CH₃N (68:32 v/v) at a flow rate of 0.8 mL/min. UV detection was performed at 254 nm. [¹⁸F]Co. No. 1 eluted at 8 min. [¹⁸F]Co. No. 1 was obtained with an average, decay-corrected, radiochemical yield of 12% respectively (relative to radioactivity of [¹⁸F]F⁻ in the preparative chromatogram, n=6). Their radiochemical purity was examined using HPLC on an analytical C₁₈ column and was more than 99%. [¹⁸F]Co. No. 1 was obtained within a total synthesis time of 60 min, and collected with an average specific radioactivity of 85 GBq/pmol at the end of synthesis (EOS, n=6).

D. Analytical Part

Melting Points

Values are either peak values or melt ranges, and are obtained with experimental uncertainties that are commonly associated with this analytical method.

For a number of compounds, melting points were determined with a DSC823e (Mettler-Toledo) (indicated as DSC). Melting points were measured with a temperature gradient of 10° C./minute. Maximum temperature was 300° C.

For a number of compounds, melting points were determined in open capillary tubes on a Mettler Toledo MP50. Melting points were measured with a temperature gradient of 10° C./minute. Maximum temperature was 300° C. The melting point data was read from a digital display and checked from a video recording system.

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl), the reported value is the one obtained for the lowest isotope mass. All results were obtained with experimental uncertainties that are commonly associated with the method used. Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

TABLE 1a

LCMS Method codes (Flow expressed in mL/min; column temperature (T) in ° C.; Run time in minutes)

| Method No. | Instrument | Column | Mobile phase | Gradient | Flow — Col T | Run time (min) |
|---|---|---|---|---|---|---|
| 1 | Waters: Acquity ® UPLC ®-DAD and SQD | Waters: HSS T3 (1.8 μm 2.1*100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.7 — 55 | 3.5 |
| 2 | Waters: Acquity ® UPLC ®-DAD and SQD | Waters: BEH C18 (1.7 μm, 2.1*50 mm) | A: 1.0 mM CH$_3$COONH$^4$ in 95% H$_2$O + 5% CH$_3$CN B: CH$_3$CN | From 95% A to 5% A in 1.3 min, held for 0.7 min | 0.8 — 55 | 2 |
| 3 | Agilent: 1100-DAD and MSD | YMC: Pack ODS-AQ (3μm, 4.6 × 50 mm) | A: HCOOH 0.1% in water, B: CH$_3$CN | 95% A to 5% A in 4.8 min, held for 1 min, back to 95% A in 0.2 min. | 2.6 | 6 |
| 4 | Agilent 1290 Infinity DAD TOF-LC/MS G6224A | YMC-pack ODS-AQ C1.8 (50 × 4.6 mm, 3μm) | A: 0.1% HCOOH in H$_2$O B: CH$_3$CN | ISET 2V1.0 Emulated Agilent Pump G131.2A V1.0 From 94.51% A to 5% A in 4.8 min, held for 1.0 min, to 95% A in 0.2 min | 2.6 35 | 6.0 |
| 5 | Waters: Acquity ® UPLC ® DAD and SQD | Waters: BEM C18 (1.7 μm, 2.1*50 min) | A: 10 mM CH$_3$COONH$_4$ in 95% H$_2$O 5% CH$_3$CN B: CH$_3$CN | From 95% A to 5% A in 1.3 min, held for 0.2 min, to 95% A in 0.2 min held for 0.1 min | 0.7 — 70 | 1.8 |

TABLE 1b

Analytical LCMS data—$R_t$ means retention time (in minutes), [M + H]$^+$ means the protonated mass of the compound, method refers to the method used for (LC)MS analysis.

| Co. No | mp (° C.) | Rt | [M + H]$^+$ | [M − H]$^-$ | LCMS Method |
|---|---|---|---|---|---|
| I-2 | | 0.94 | 281.2 | 279.1 | 2 |
| 1 | 182.53° C. (DSC)* | 1.84 | 254.2 | 252.1 | 1 |
| 2 | 203.3° C. | 2.073 | 254.0 | | 3 |
| 3 | 208.5° C. | 1.878 | 268.0 | | 3 |
| 4 | 173.1° C. | 1.772 | 270.0 | | 3 |
| 5 | 191.4° C. | 1.413 | 283.2 | | 4 |
| 6 | 146.3° C. | 1.647 | 297.2 | | 4 |
| 7 | 285.1° C. | 1.533 | 297.2 | | 4 |
| 8 | | 1.758 | 311.2 | | 4 |
| 9 | 104.6° C. | 1.72 | 284.2 | 282.2 | 5 |
| 10 | 249.3° C. | 1.947 | 298.2 | | 4 |

*from 30 to 300° C. at 10° C./min 50 mL N$_2$

CHN Determinations & Water Determinations

For a number of compounds, amount of Carbon. Hydrogen and Nitrogen (CHN) in (% w/w) was determined by Dynamic Flash Combustion on an EA 1108 CHN analyzer from Fisons instruments.

For a number of compounds, water (% w/w) was determined with a CA-02-moisture meter (Mitsubishi) Coulometric principle applied to Karl Fischer titration.

TABLE 1c

CHN and water determinations.

| Co. No. | C (% w/w) | H (% w/w) | N (% w/w) | H$_2$O (% w/w) |
|---|---|---|---|---|
| 1 | 70.52 | 4.95 | 16.79 | |
| I-2 | 57.63 | 3.96 | 15.07 | 0.42 |

E. Biological Part
Materials and Methods
General

Quantification of radioactivity in samples of biodistribution and radiometabolite studies was performed using an automated γ-counter equipped with a 3-inch NaI(Tl) well crystal coupled to a multichannel analyzer, mounted in a sample changer (Wallac 2480 Wizard 3q, Wallac, Turku, Finland). The values are corrected for background radiation, physical decay and counter dead time. Rodents were housed in individually ventilated cages in a thermo-regulated (~22° C.), humidity-controlled facility under a 12 h-12 h light-dark cycle, with access to food and water ad libitum. All animal experiments were conducted according to the Belgian code of practice for the care and the use of animals, after approval from the university animal ethics committee.

Aggregated Tau and Amyloid Plaques Isolation from Human Ad Brain

Enriched aggregated tau fractions were prepared according to a slightly modified version of the protocol described by Greenberg and Davies (Greenberg S. G., Davies P. A preparation of Alzheimer paired helical filaments that displays distinct T proteins by polyacrylamide gel electrophoresis. Proc. Natl. Acad. Sci. 1990; 87: 5827-5831) using human AD brain tissue (occipital cortex with high tau fibril load). Briefly, frozen human AD brain samples (~10 g) were homogenized with 10 vol of cold homogenization buffer (10 mM Tris, 800 mM NaCl, 1 mM EGTA, 10% sucrose, pH 7.4 containing PhosSTOP phosphatase and cOmplete EDTA-free protease inhibitor (Roche, Vilvoorde, Belgium)) on ice. After centrifugation at 27 000×g for 20 min at 4° C. the supernatant was recovered and 1% (w/v) N-lauroylsarcosine and 1% (v/v) 2-mercaptoethanol were added. The N-lauroylsarcosine/2-mercaptoethanol supernatant was incubated for 2 h at 37° C. while shaking on an orbital shaker. Subsequently, ultracentrifugation at 108 000×g for 1.5 h at room temperature enriched aggregated tau in the pellet. Supernatant was removed and the pellet was carefully rinsed twice with a small amount of TBS (50 mM Tris, 150 mM NaCl, pH 7.4). Finally, the aggregated tau pellet was recovered in TBS and resuspended to ensure sample homogeneity. Small aliquots were stored at −80° C.

Enriched aggregated β-amyloid preps were prepared from frozen human AD brain samples (10 g—occipital cortex with high amyloid plaques load) that were homogenized with 7-fold vol of cold homogenization buffer (250 mM sucrose, 20 mM Tris base, 1 mM EDTA, 1 mM EGTA and PhosSTOP phosphatase and cOmplete EDTA-free protease inhibitor) on ice. After centrifugation at 27 000×g for 20 min at 4° C. cell debris was removed. Supernatant containing amyloid plaques was aliquoted and stored at −80° C.

In Vitro Competitive Radioligand Binding Assays

The competitive radioligand binding assays measure the binding of a radiolabeled reference ligand in the presence of a dose response concentration range of test compounds.

Briefly, aggregated tau preps were diluted to 100 μg protein/ml in PBS buffer with 5% ethanol. In a 96-well format, $^3$H-T808 (specific activity; 32.97 Ci/mmol) was added at a final concentration of 10 nM to increasing amounts of test compound in the presence of 20 μg protein of aggregated tau prep. Nonspecific binding was defined as the number of counts remaining in the presence of 50 μM Thioflavin T (common beta sheet binder). After 2 h incubation at room temperature, the unbound ligand is removed by filtration of the binding mixtures over GF/B glass filters using a Filtermate 96 harvester instrument (Perkin Elmer, Zaventem, Belgium). The filters were washed three times with PBS buffer containing 20% ethanol. After overnight drying of the filter plate, Microscint O liquid (Perkin Elmer) was added and the amount of radiolabeled ligand bound to the fibrils is measured by liquid scintillation counting in a Topcount instrument (Packard Instrument Company, Connecticut, USA).

Values for half-maximal inhibitory concentration (IC$_{50}$) were determined from displacement curves of at least two independent experiments using GraphPad Prism software (GraphPad Software, San Diego, CA).

To determine compound binding to aggregated β-amyloid a similar assay was put in place but with some minor modifications. Briefly, amyloid preps were diluted to 150 μg protein/ml in 50 mM Tris with 0.1% BSA and 5% ethanol. $^3$H-AV-45 (florbetapir-specific activity, 45.95 Ci/mmol) was added at a final concentration of 10 nM to increasing amounts of test compound in the presence of 30 μg protein of amyloid plaques prep. Nonspecific binding was determined in the presence of 500 μM Thioflavin T. After 150 min incubation at room temperature, the binding mixtures were filtered over GF/B glass filters. The filters were washed three times with PBS buffer containing 20% ethanol. Subsequent steps were identical to those described for the aggregated tau preps.

[$^{19}$F]-Co. No. 1 showed potent binding (pIC$_{50}$ 8.24, corresponding to a K$_i$ of 2.4 nM) to extracted human tau using [$^3$H]-T808 and weak binding to extracted human amyloid-beta aggregates (pIC$_{50}$ 5.18, corresponding to a K$_i$ of 3.2 μM) using [$^3$H]-AV-45 in this radiolabel displacement assay.

Immunohistochemistry (IHC): M&M Human Brain

Human AD brain blocks (Braak stage V-VI) were snap-frozen, sliced with a cryostat (20 μm thickness) and stored at −80° C. until used for immunohistochemistry. Slices were dried, fixed in formalin and incubated with hydrogen peroxide (DAKO, S2023) for 5 minutes and blocking reagent (PBS1×+0.05% Triton X-100) during 1 hour. Anti-amyloid or anti-tau antibody [(4G8, Covance, SIG-38220), 1/500 dilution in antibody diluent with background reducing components (DAKO, S3022) or (AT8 (Bierna et al., EMBO J. 1992, 11(4):1593-7), in-house, 1 mg/ml stock concentration), 0.2 μg/mL in antibody diluent with background reducing components (DAKO, S3022)], was applied to the slices for 1 hour. The striatal tissue was immunolabeled with anti-MAO-B and anti-MAO-A antibodies (1:100, Thermo Fisher) to confirm MAO expression. After extensive washing, slides were incubated with HRP-conjugated anti-mouse secondary antibody (Envision, DAKO, K4000), followed by chromogenic DAB labelling (DAKO, K3468). After counterstaining with hematoxylin, slices were dehydrated and mounted with organic mounting medium (Vectamount, Vector labs, H-5000). FIG. 1c shows β-amyloid pathology in AD brain as detected with 4G8 IHC and FIG. 1b shows tau pathology in AD brain as detected with AT8 IHC.

Autoradiography Studies a) Air-dried frozen, 10-μm-thick slices of the visual cortex of an AD-patient (68-year old female with Braak stage V-VI) were incubated for 60 min with [$^{18}$F]Co. No. 1 (7.4 kBq/500 μL per slice) and subsequently washed with mixtures of PBS and ethanol as described elsewhere (Xia C. F., Arteaga J., Chen G., et al. Alzheimer's Dement. 2013, 1-11). To assess specificity of binding, slices were incubated with tracer in the presence of 1 μM of authentic T808 or Co. No. 1. After drying, slices were exposed to a phosphor storage screen (super-resolution screen, Perkin Elmer). Screens were read in a Cyclone Plus system (Perkin Elmer, Waltham, MA, U.S.A.) and analyzed using Optiquant software. Results are expressed as digital light units per square mm (DLU/mm$^2$). Adjacent AD slices were immunostained with anti-tau (AT8) and anti-Aβ antibodies (4G8), to correlate with [$^{18}$F]Co. No. 1 binding.

Figure 2:
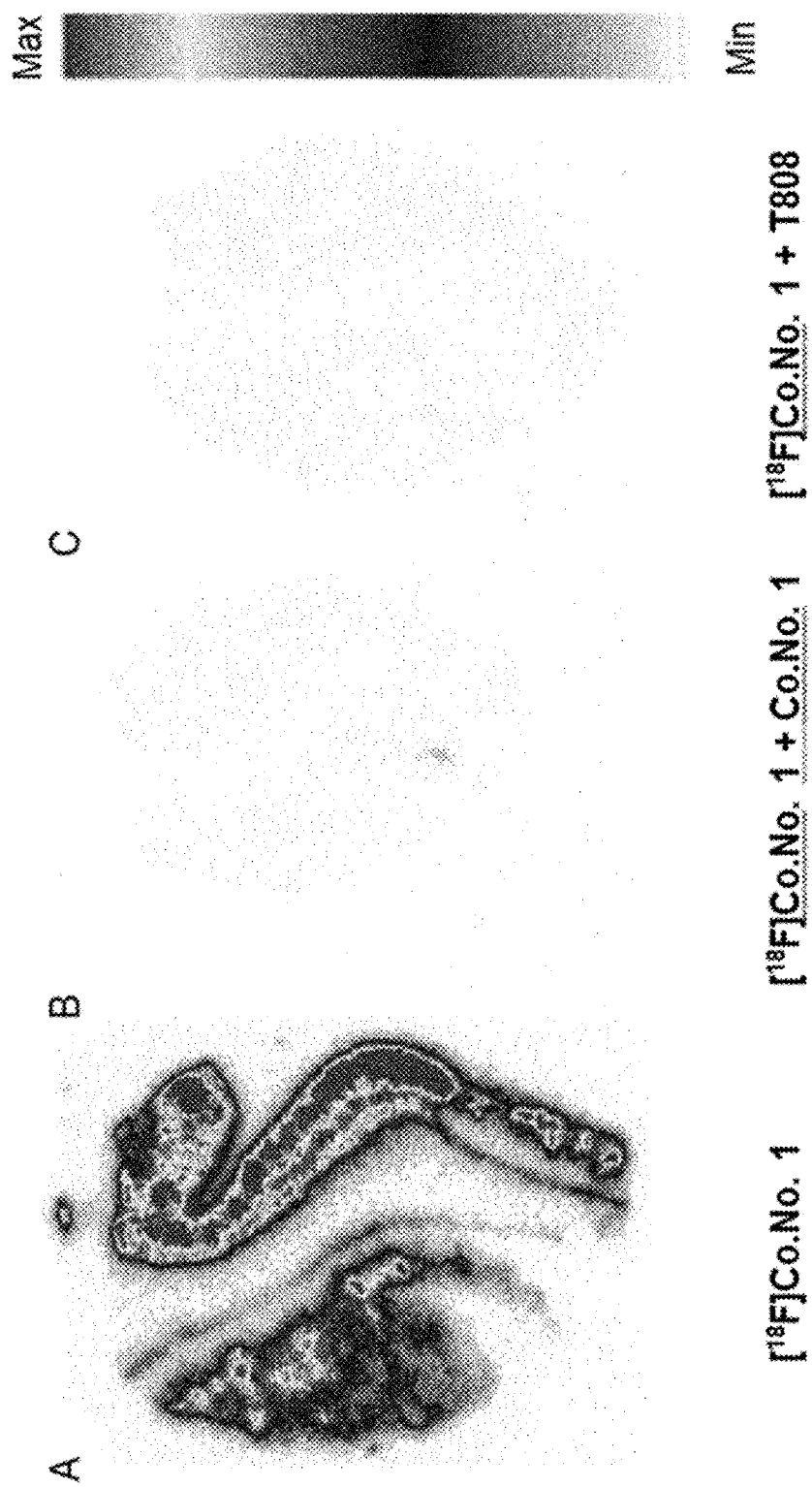
FIG. 2 shows a comparison between the ARG shown in FIG. 1 (A), and adjacent human AD brain slices incubated with [$^{18}$F]Co. No. 1 (7.4 kBq/500 µL/slice) in the presence of authentic reference compound Co. No. 1 (B) or T808 (C) at 1 µmol/L.

Digital autoradiography with [$^{18}$F]Co. No. 1 on human AD-slices showed high and selective binding to cortical tau-rich regions (FIG. 1, A). Immunohistochemistry with tau and Aβ antibodies, performed on adjacent slices, identified numerous NFT and neuritic plaque deposits, confirming co-localization of tracer binding with NFTs (FIG. 1, respectively B and C). To assess the specificity of the tracer binding to these NFTs, blocking studies with authentic reference compound Co. No. 1 and the structurally unrelated reference compound T808 were performed (FIG. 2). Self-block with cold Co. No. 1 resulted in 99% inhibition, which demonstrates that binding of [$^{18}$F]Co. No. 1 is specific. Binding of [$^{18}$F]Co. No. 1 was reduced with 99% in the presence of 1 μM T808, indicating tau-specific binding, since T808 was reported with high affinity ($K_D$=22 nM) for aggregated tau and high selective for tau over Aβ aggregates (27-fold) (Zhang W., Arteaga J., Cashion D. K. et al. *J Alzheimers Dis.* 2012, 31(3), 601-612).

b) [$^3$H]-Co. No. 1 binds to frozen slices of AD brain containing tau and Aβ pathology, but does not bind tau pathology negative AD tissue containing only Aβ plaques (FIG. 3D, E). The tracer was tested at 10 nM and higher concentrations were not investigated in this study. Importantly, [$^3$H]-Co. No. 1 also shows no binding to MAO-rich human tissue (striatum) (FIG. 3A). These data support that our compound is selective for tau pathology over Aβ pathology and MAO.

In comparison, the tau tracer [$^3$H]-THK-5351 and the Aβ tracer [$^3$H]-AV-45 were used as THK-5351 is known to also bind MAO. These experiments show that 10 nM of [$^3$H]-THK-5351 binds to MAO-rich human tissue and this binding can be self-blocked by 10 μM THK-5351 (cold), but also by 10 μM Co. No. 1 (cold) (FIG. 3F-H). This indicates that Co. No. 1 at higher concentrations can bind MAO.

[$^3$H]-THK5351 also binds to AD tissue containing only Aβ plaques (tau negative) and thus confirms the low selectivity of THK-5351 (FIG. 3I, J).

Figure 3:
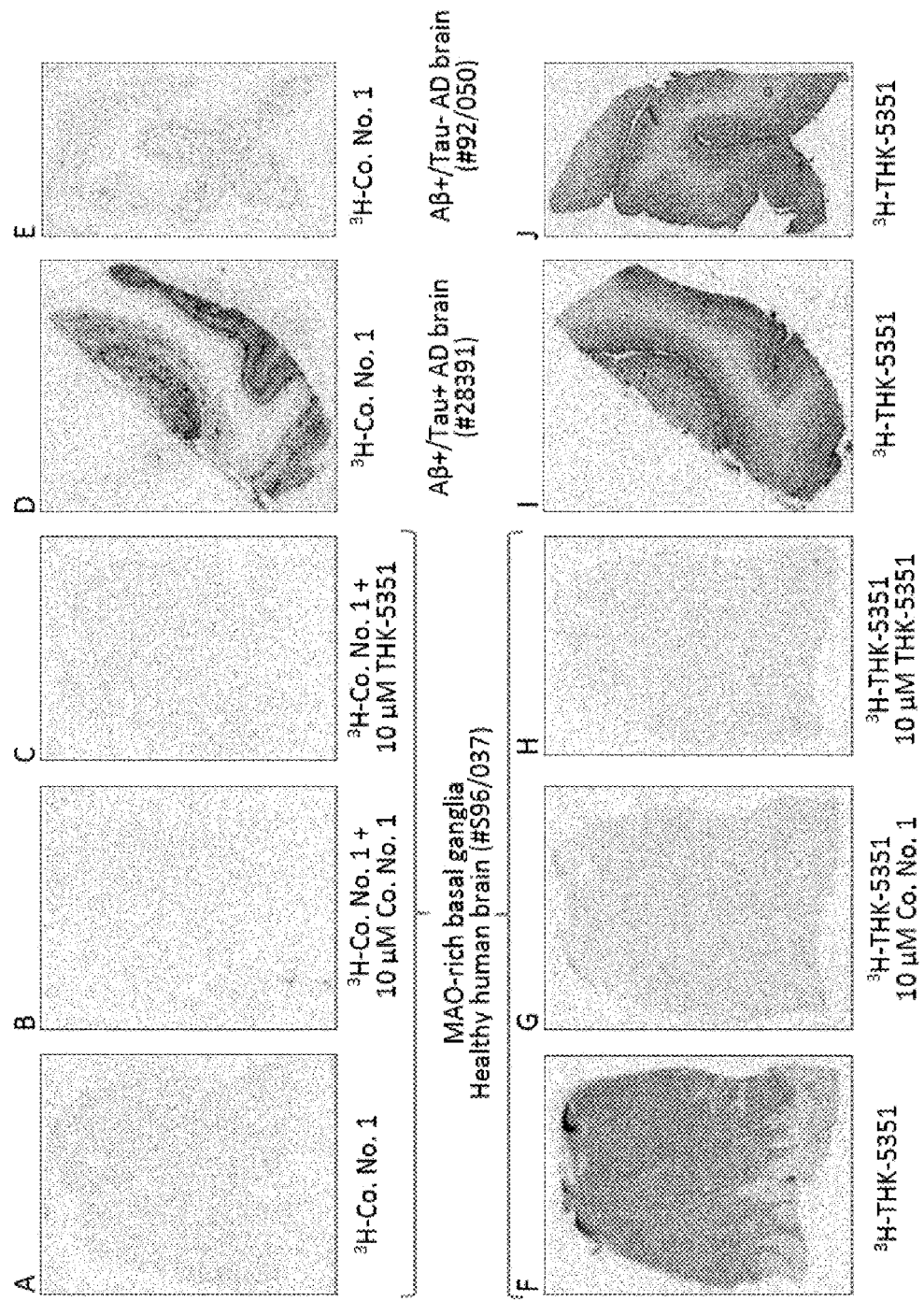
FIG. 3 shows incubation with 10 nM [$^3$H]Co. No. 1 on human basal ganglia (striatal) tissue (A), followed by treatment with 10 µM Co. No. 1 (B) or 10 µM THK5351 (C).
Figure 3:
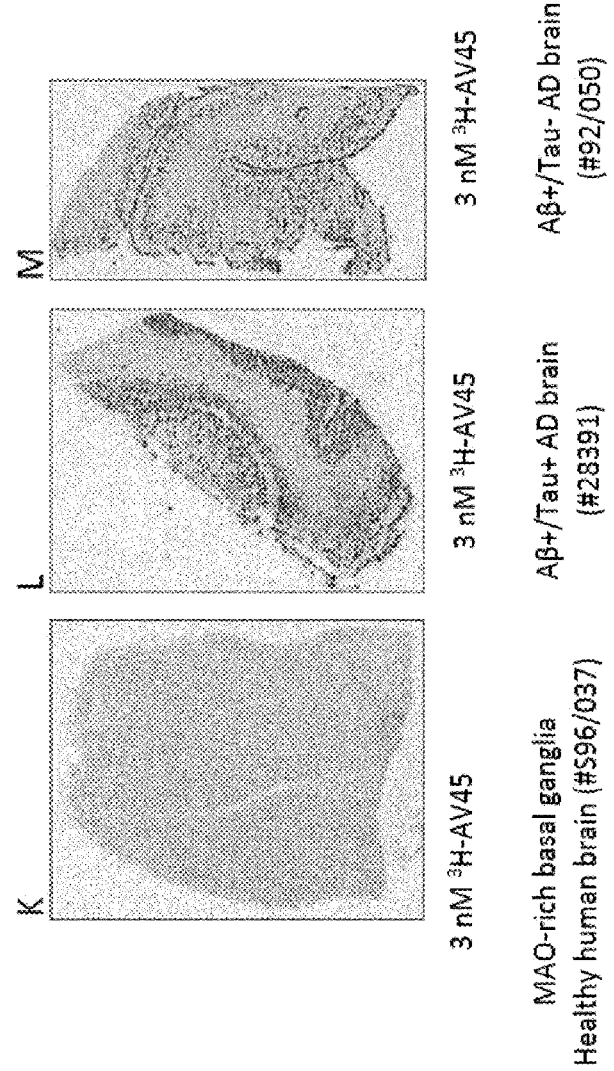
Figure 5:
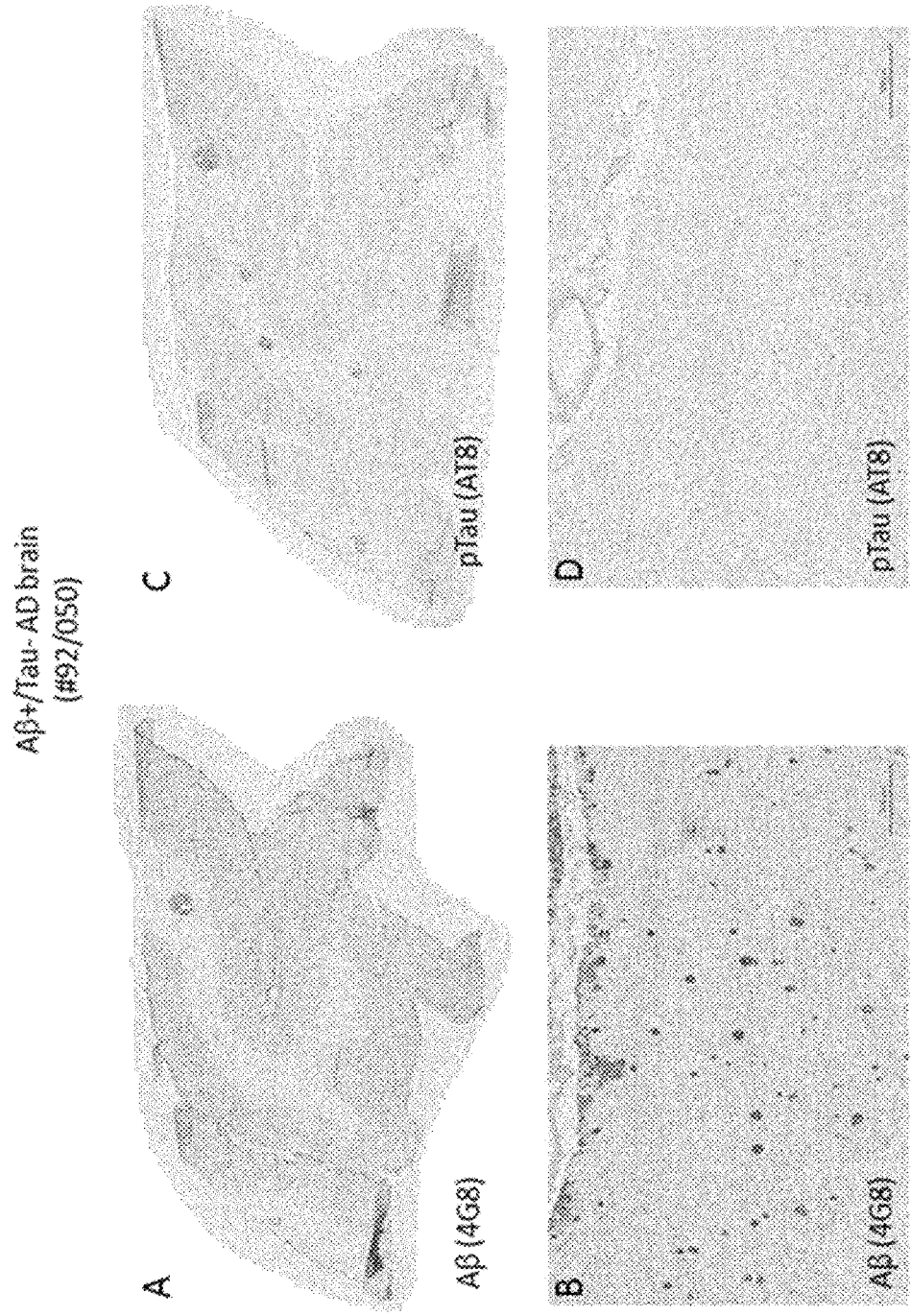
FIG. 5 shows an adjacent human AD brain slice (lateral-occipital gyrus, female) to the one used in FIG. 3E and FIG. 3J. The presence of β-amyloid plaques (A, B) and absence of tau tangles (C, D) was confirmed with immunohistochemistry using respectively 4G8 and AT8 antibodies.
Figure 7:
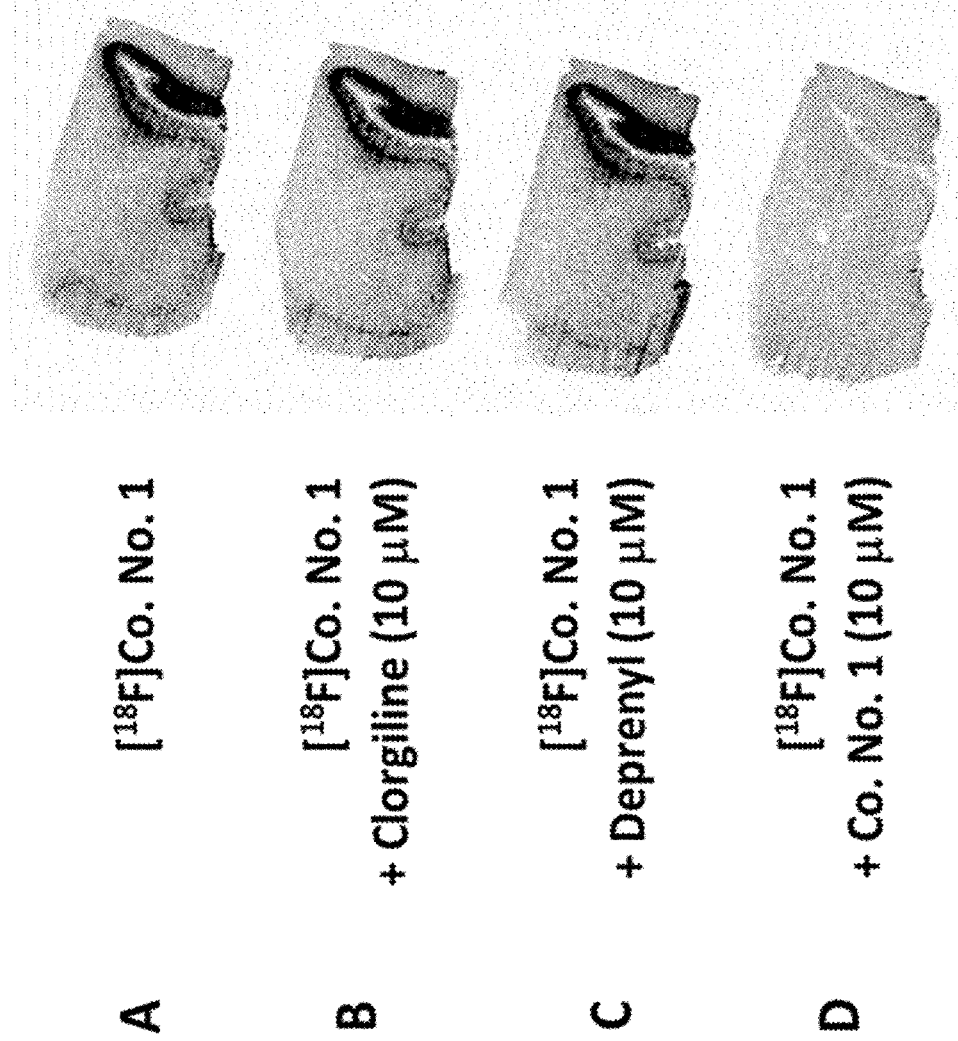
FIG. 7 shows incubation with 0.2 mCi/mL [$^{18}$F]Co. No. 1 on human AD tissue slices (parieto-temporal cortex, Braak stage VI) (A), and treatment with 10 µM Clorgiline (B), 10 µM Deprenyl (C) and 10 µM Co. No. 1 (D).
Figure 8:
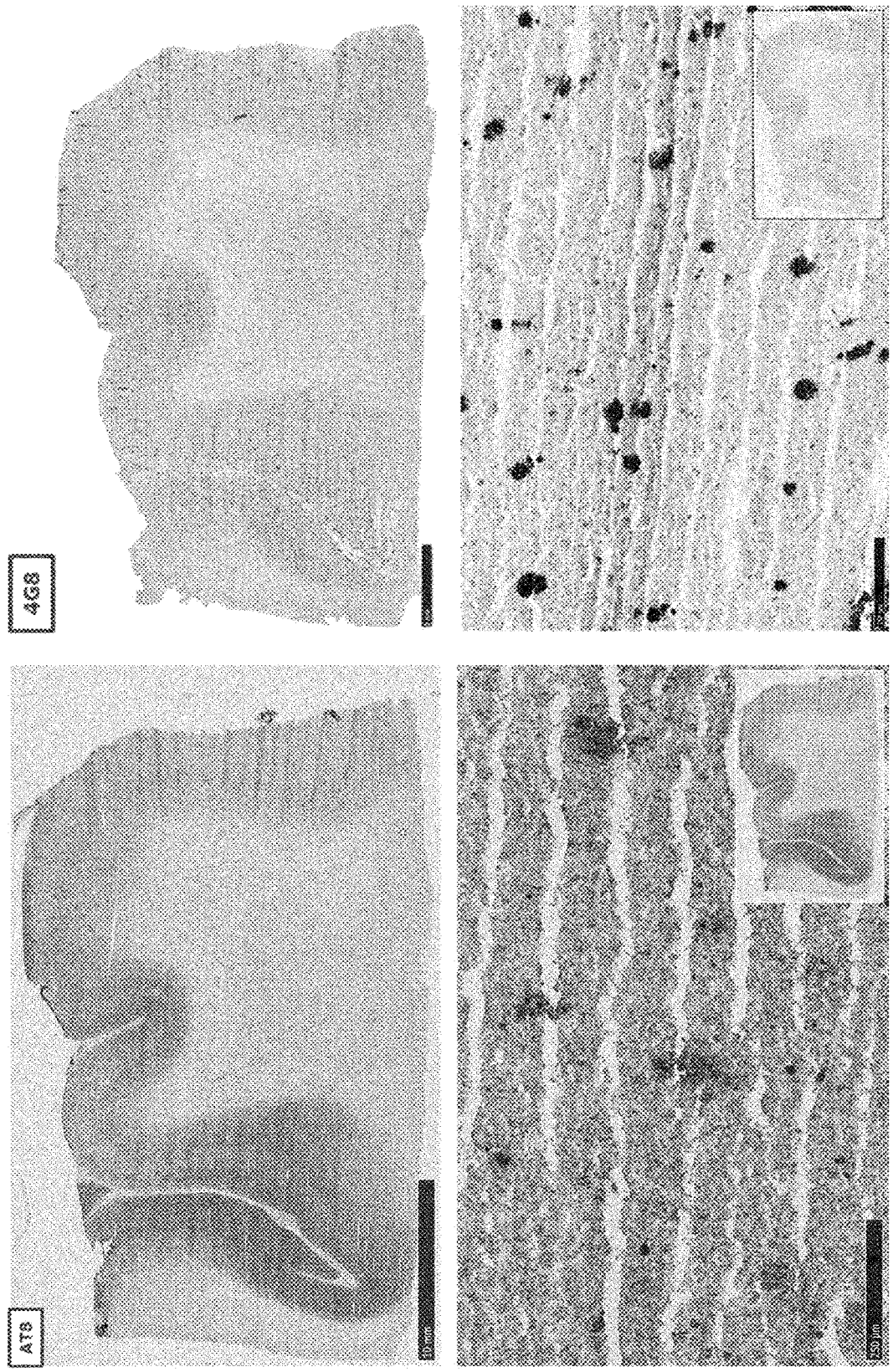
FIG. 8 shows AT8 and 4G8 IHC of respectively tau and amyloid pathology in adjacent AD brain slices (parietal-temporal cortex, Braak stage VI) to the ones referred to in FIG. 7.

[$^3$H]-AV-45 (selective for Aβ plaques) binds both tau and Aβ pathology (Aβ+/tau+, Tissue #28391) and Aβ pathology only (Aβ+/tau−, Tissue #92/050) human tissues as expected (FIG. 3L-M). As a control for the human AD tissues (Tissue #28391: FIG. 4, Tissue #92/050: FIG. 5) and striatal tissue (FIG. 6) used in this study immunohistochemistry was performed. The human AD tissues (#28391: #92/050) were immunolabeled with 4G8 (anti-amyloid antibody) and AT8 (anti-tau antibody) and clearly demonstrate that slices from #28391 are Aβ+/tau+, whereas slices from #92/050 are Aβ+/tau− (FIGS. 4 and 5). Furthermore, MAO-B and MAO-A expression in the human striatal tissue (#S96/037) was confirmed using immunohistochemistry (FIG. 6). These data support the conclusions from the in vitro binding observed in FIG. 3.

c) Binding of [$^{18}$F] Co. No. 1 to human AD tissue was assessed in the presence of reported MAO binders. As can be seen in FIG. 7, 0.2 mCi/mL of [$^{18}$F] Co. No. 1 showed strong binding to tau pathology in these human AD slices (FIG. 7A). This binding pattern was maintained when the sample was incubated with 10 μM of clorgiline, a strong irreversible MAO binder with moderate selectivity for the A-subtype (FIG. 7B), or 10 μM selegiline (=deprenyl), a strong irreversible MAO-B binder (FIG. 7C). The binding of [$^{18}$F] Co. No. 1 could be entirely blocked with 10 μM of authentic Co. No. 1 (FIG. 7D). Adjacent AD slices were immunostained with anti-tau (AT8) and anti-Aβ (4G8) antibodies to correlate with [$^{18}$F]Co. No. 1 binding (FIG. 8).

MicroPET Imaging STUDIES

Wistar Rats

A dynamic 120-min μPET scan with [$^{18}$F]Co. No. 1 or [$^{18}$F]T807 was acquired on a Focus 220 μPET scanner (Concorde Microsystems, Knoxville, TN, U.S.A.) on three female Wistar rats simultaneously. The rats were kept under gas anaesthesia during the whole procedure (2.5% isoflurane in O$_2$ at 1 L/min flow rate). Scans were acquired in list mode and acquisition data were Fourier rebinned in 24 time frames (4×15 s, 4×60 s, 5×180 s, 8×300 s, 3×600 s). Data, which were 3D maximum a posteriori (3D-MAP) reconstructed, were manually aligned with a rat brain $^{18}$F-FDG template in Paxinos coordinates using an affine transformation, to allow predefined volumes of interest (VOIs) analysis (Casteels C., et al. *J. Nucl. Med.* 2006, 47, 1858-1866). Time-activity curves (TACs) of the whole brain were generated using VOIs with PMOD software (v 3.2, PMOD Technologies, Zürich, Switzerland). Radioactivity concentration in the brain was expressed as standardized uptake value (SUV, calculated as (radioactivity in Bq in brain/mL)/(total injected dose (Bq)/body weight in g)) as a function of time after tracer injection. Scans were started immediately after IV injection of about 50 MBq radiotracer (n=3/tracer). For pre-treatment and displacement studies, cold reference compound Co. No. 1 or T807 was dissolved in a mixture of 5% DMSO, 5% Tween 80 and 40% (2-hydroxypropyl)-β-cyclodextrin, filtered through a 0.22-μm membrane filter (Millex-GV. Millipore) prior to injection. Pre-treatment (n=1) was done by subcutaneous (SC) injection of 10 mg/kg of Co. No. 1 or T807, 60 min prior to radiotracer injection. Displacement (n=1) was performed by IV injection of 1 mg/kg Co. No. 1 or T807 30 min after radiotracer injection. μPET images were compared to a baseline scan (n=1), acquired in a non-treated rat.

Figure 9:
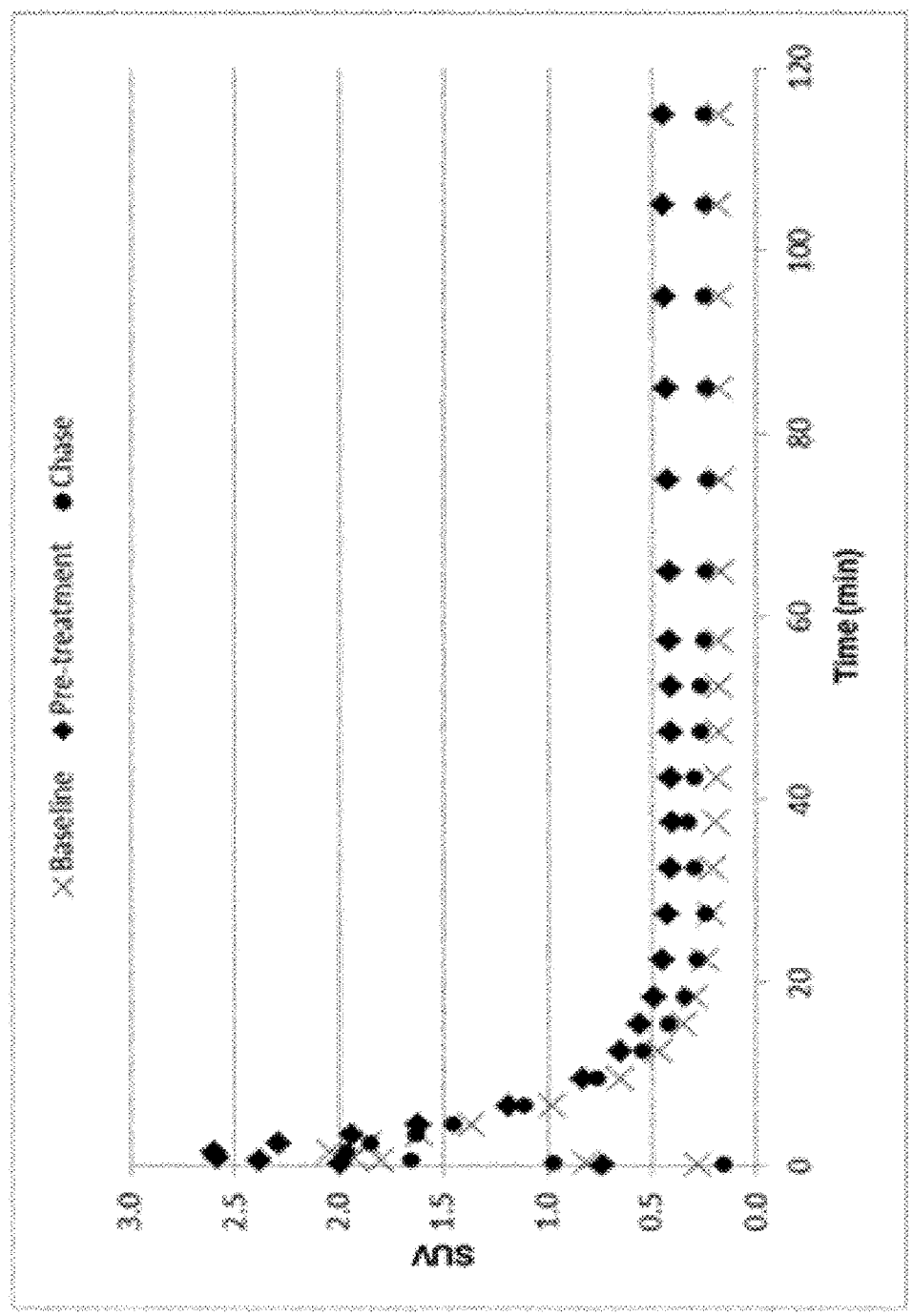
FIG. 9 shows µPET time-activity curves expressed as standardized uptake values (SUV) for [$^{18}$F]Co. No. 1
Figure 10:
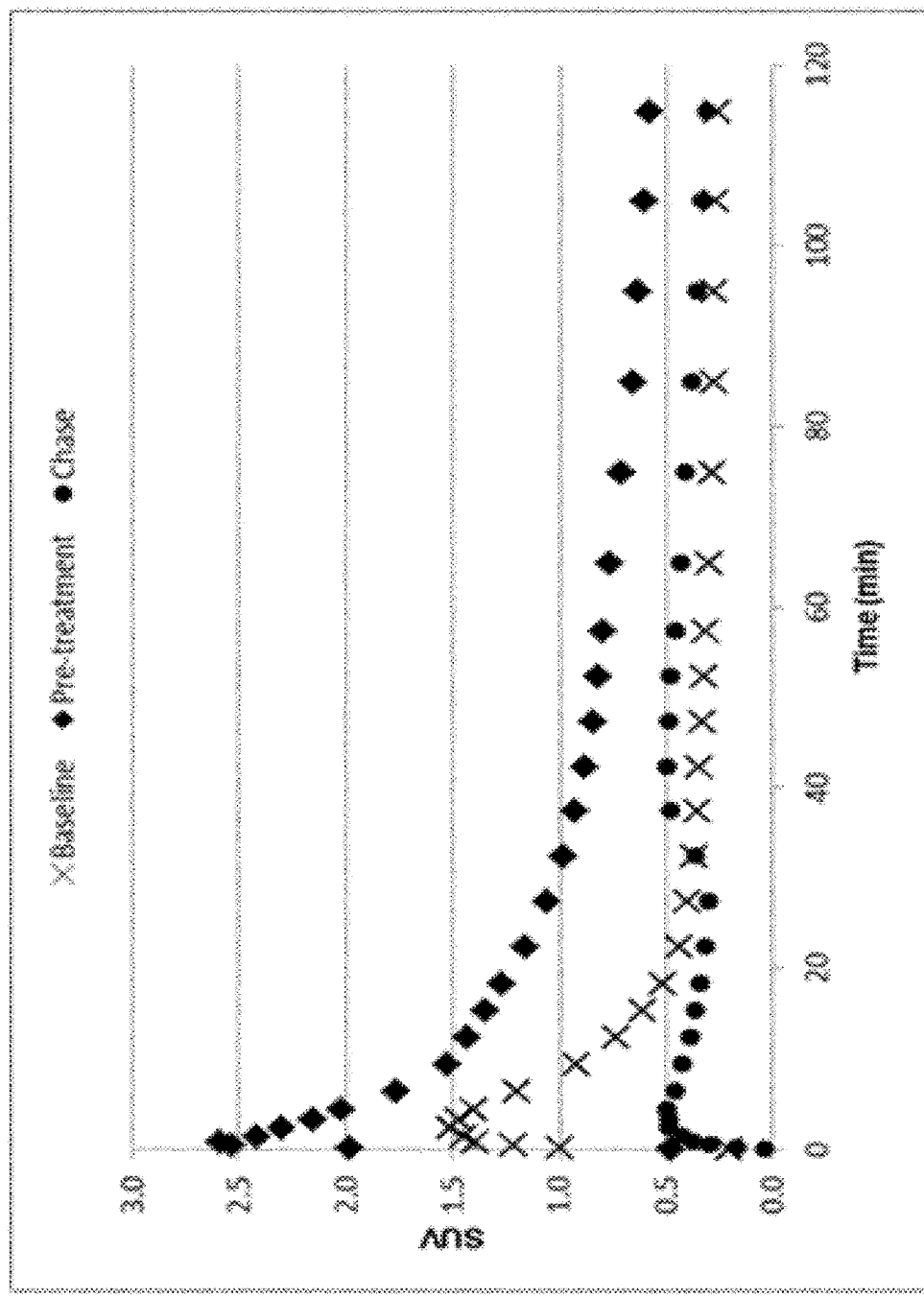
FIG. 10 shows µPET time-activity curves for [$^{18}$F]T807 (C) in the whole brain of three female Wistar rats. Three separate studies are shown: a baseline scan (only tracer), a pre-treatment experiment (cold Co. No. 1 or T807, 10 mg/kg injected subcutaneously 60 min prior to radiotracer injection), and a chase study (cold Co. No. 1 or T807, 1 mg/kg injected intravenously 30 min after radiotracer injection).
Figure 11:
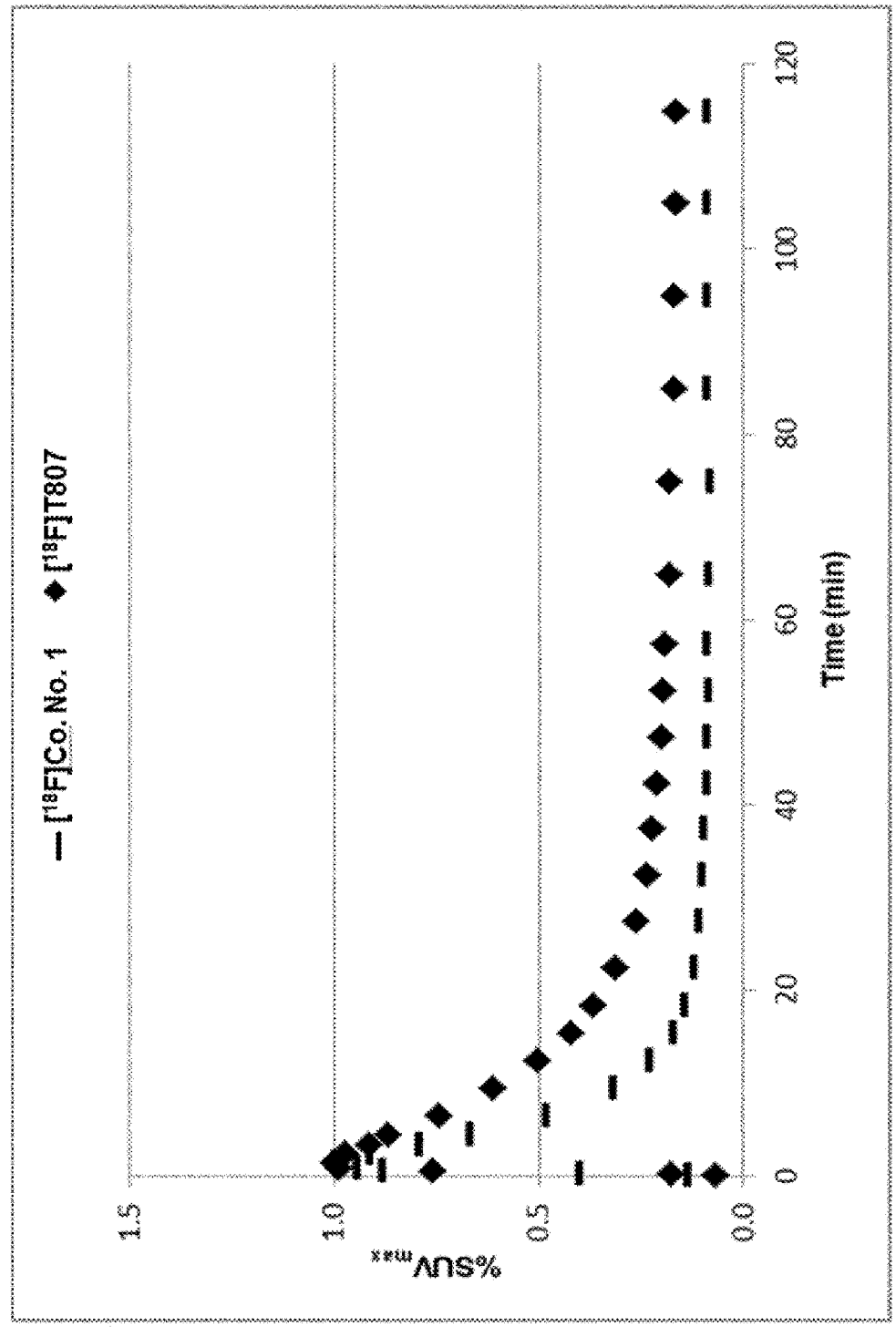
FIG. 11 shows % $SUV_{max}$ curves of small animal PET time-activity curves of [$^{18}$F]Co. No. 1 and [$^{18}$F]T807 in the total brain of a Wistar rat.

Results of the 120-min baseline, pretreatment and chase study of [$^{18}$F]Co. No. 1 and benchmark compound [$^{18}$F]T807 are shown in FIGS. 9-11 (time activity curves, TACs and % SUV$_{max}$). TACs of the baseline scans of [$^{18}$F]Co. No. 1 (FIG. 9) showed high initial brain uptake with a high intensity SUV value in the brain of ~2.0, compared to ~1.8 for [$^{18}$F]T807 (FIG. 10). Bone uptake was observed at later time points for both compounds. [$^{18}$F]Co. No. 1 had a faster brain wash-out rate (SUV value of 0.2 at 60 min p.i.) compared to [$^{18}$F]T807 (SUV value of 0.4 at 60 min p.i.) as shown in the % SUV$_{max}$ curves (FIG. 11). No self-blocking or self-chase effect was observed for [$^{18}$F]Co. No. 1 indicating absence of specific not tau related binding in brain (FIG. 9). Lower brain uptake during the baseline scan of [$^{18}$F]T807, compared to the pre-treatment study was recorded, probably caused by saturation of metabolic enzymes and/or plasma proteins (FIG. 10). A similar effect was seen 40 min p.i. in the chase study.

MicroPET Imaging Studies

Rhesus Monkey

A dynamic 120-min μPET scan with [$^{18}$F]Co. No. 1 or [$^{18}$F]T807 was performed with a Focus 220 μPET scanner on a rhesus monkey (6 y-old male *Macaca mulatta*, 7.6 kg), that was sedated with ketamine (Ketalar®) and xylazine (Rompun®) via intramuscular (IM) injection. During scanning the monkey received repeatedly an additional dose of ketamine/xylazine via IV injection. O$_2$ saturation in blood, breathing frequency and heartbeat frequency were monitored during the entire experiment. The head of the animal was placed central in the field of view of the μPET scanner. Scans were acquired in list mode and Fourier rebinned in 24 time frames (4×15 s, 4×60 s, 5×180 s, 8×300 s, 3×600 s). Data were reconstructed using a 3D maximum a posteriori (3D-MAP) iterative reconstruction. TACs of the whole brain were generated using VOIs with PMOD software. Radioactivity concentration in the brain is expressed as SUV as a function of time after tracer injection. Scans were started immediately after IV injection of 185 MBq of [$^{18}$F]Co. No. 1 or [$^{18}$F]T807 via the vena saphena of the right leg. For the pre-treatment study, cold reference compound Co. No. 1 was dissolved in a mixture of 10% DMSO and 40% (2-hydroxy-propyl)-o-cyclodextrin, filtered through a 0.22-μm membrane filter (Millex-GV, Millipore) prior to injection. Pre-treatment (n=1) was done by IV co-injection of 1 mg/kg of cold Co. No. 1 and radiotracer solution. μPET images were compared to a baseline scan (n=1), acquired in the non-treated monkey.

Figure 12:
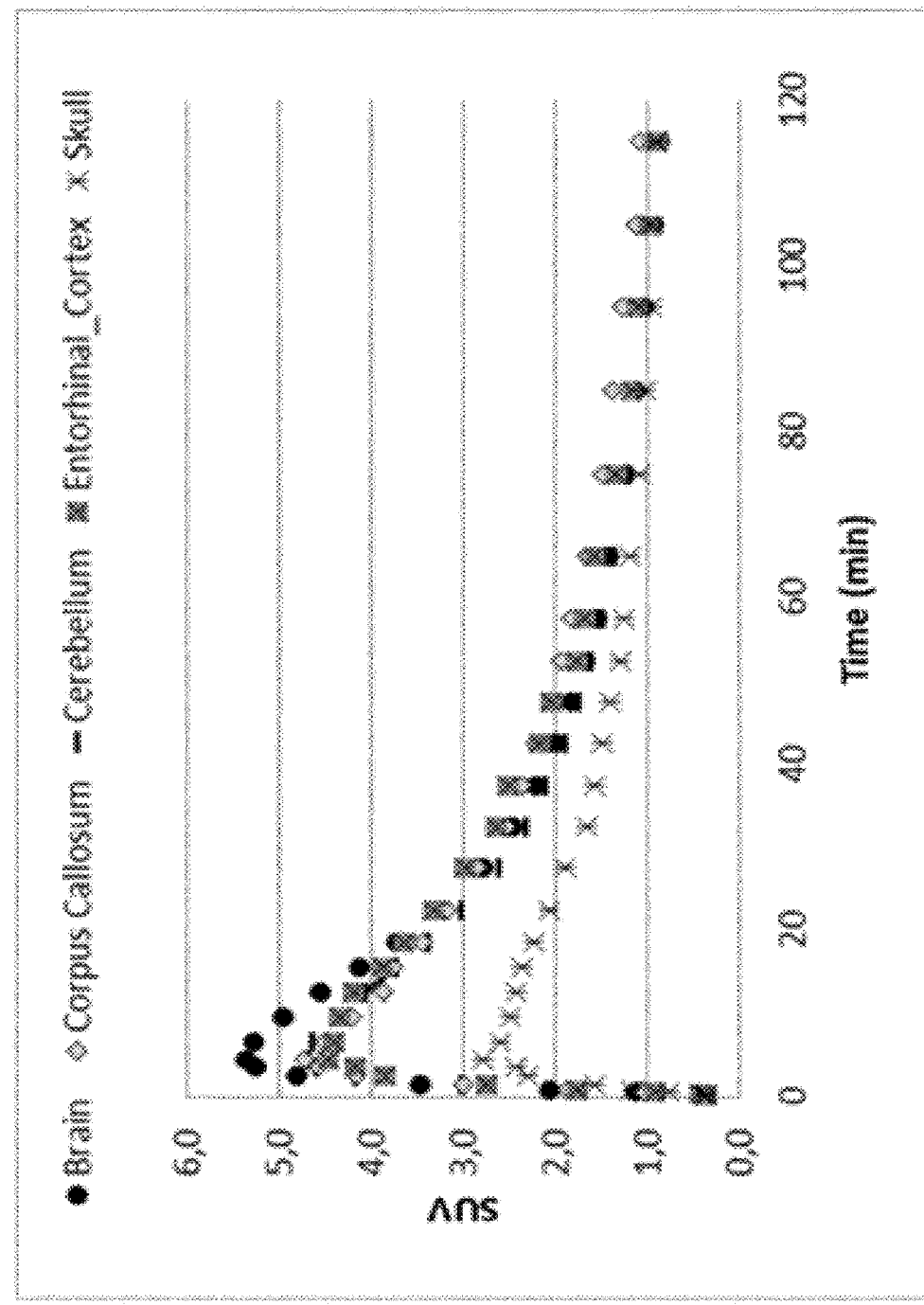
FIG. 12 shows µPET time-activity curves for [$^{18}$F]Co. No. 1
Figure 13:
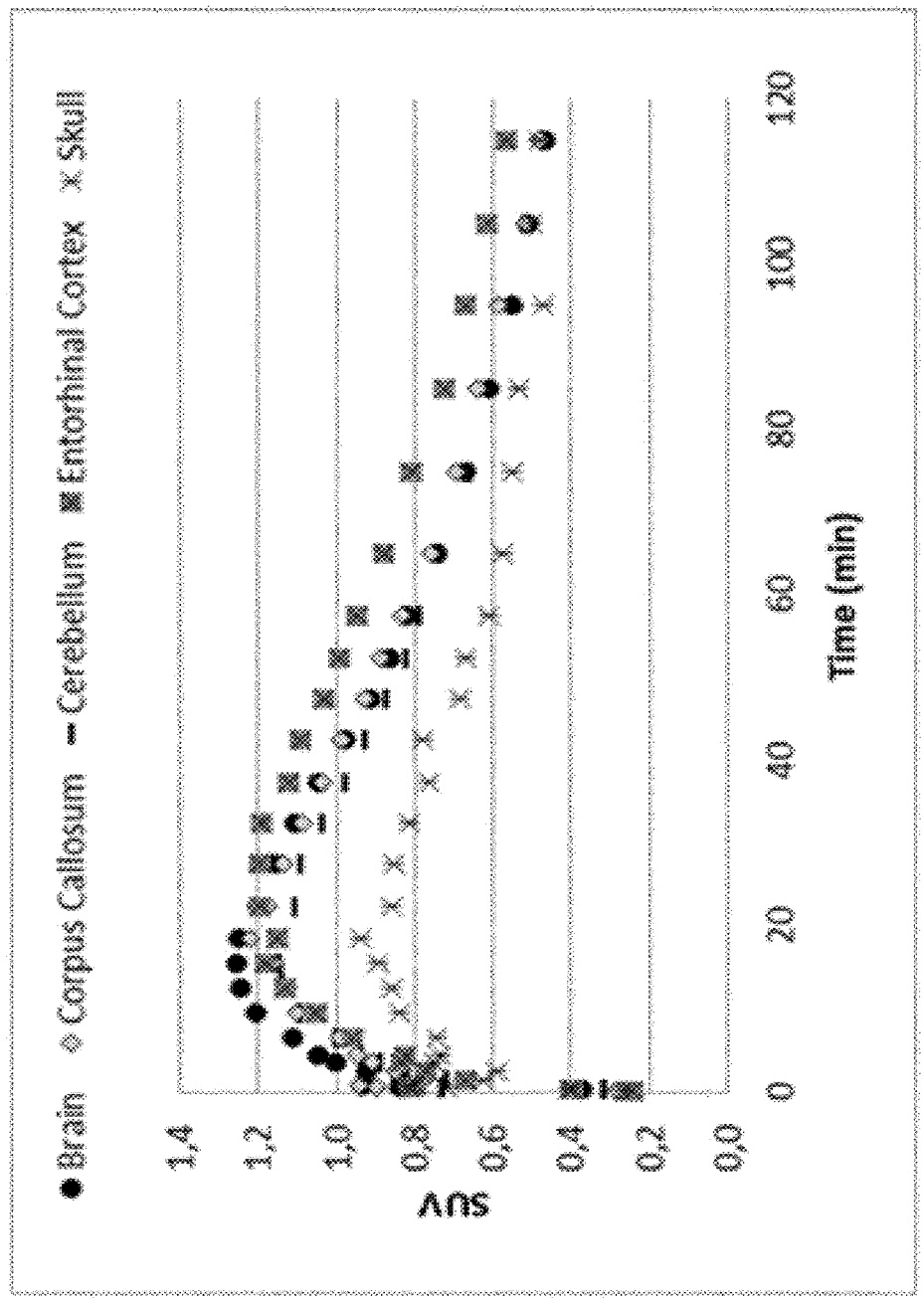
FIG. 13 shows µPET time-activity curves for [$^{18}$F]T807 in the whole brain, corpus callosum, cerebellum, enthorinal cortex and skull of a rhesus monkey.
Figure 14:
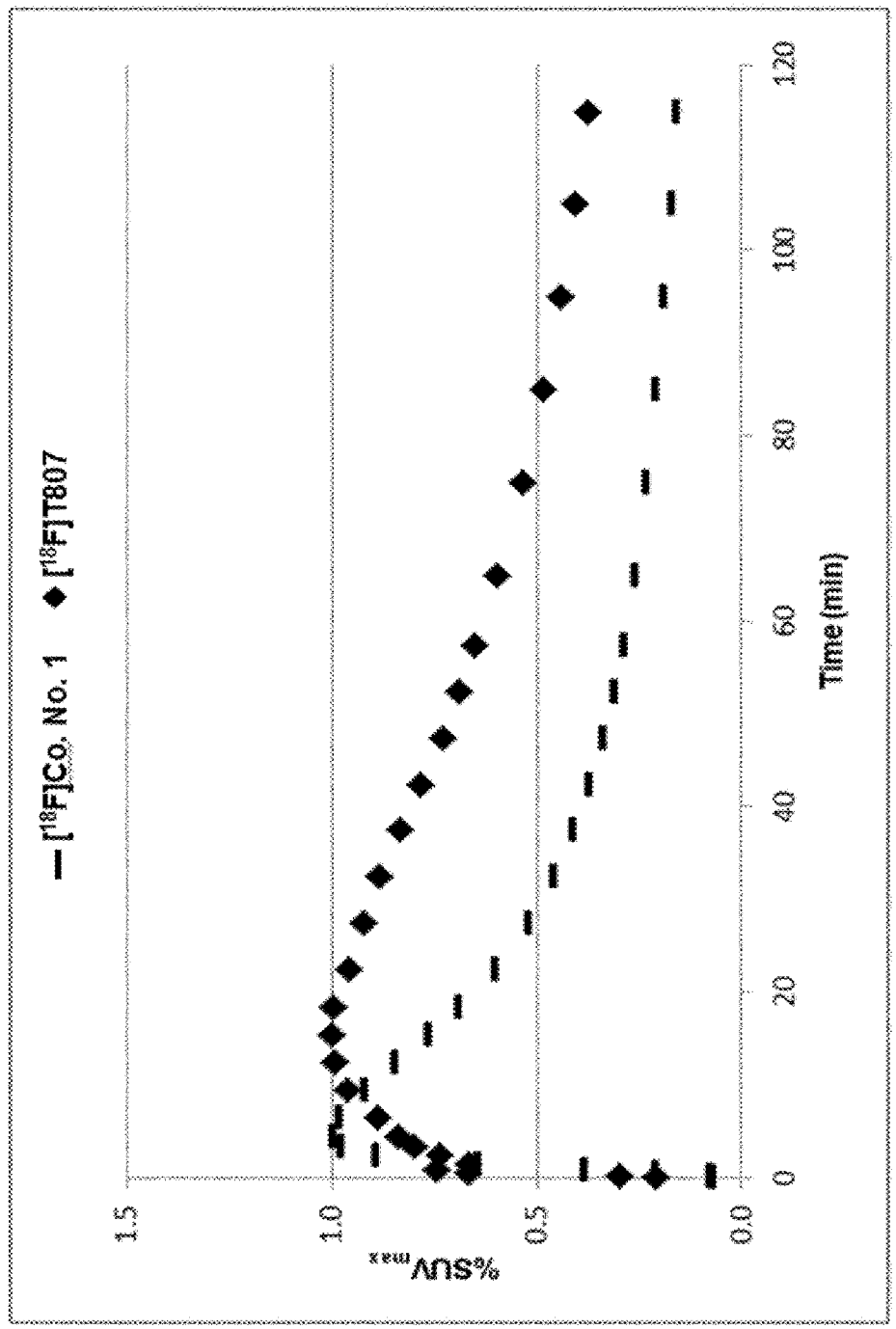
FIG. 14 shows % $SUV_{max}$ curves of small animal µPET time-activity curves of [$^{18}$F]Co. No. 1 and [$^{18}$F]T807 in the total brain of a rhesus monkey.

Results of the 120-min baseline scan of [$^{18}$F]Co. No. 1 and [$^{18}$F]T807 are shown in FIGS. 12-14 (TACs and % SUV$_{max}$). TACs of the baseline scan of [$^{18}$F]Co. No. 1 in the brain show high initial brain uptake (SUV value of ~5.4 in the total brain) with a rapid wash-out (FIG. 12). TACs of the baseline scan of [$^{18}$F]T807 in the brain show a slower initial brain uptake (SUV value of ~1.3) and wash-out (FIG. 13). A homogeneous distribution of [$^{18}$F]Co. No. 1 was recorded in all observed brain regions, with no increased uptake in the corpus callosum. TACs at the side of the skull show that there was no free $^{18}$F-fluoride bone uptake observed 120 min p.i., since the SUV signal did not increase as a function of time.

The invention claimed is:

1. A compound according to Formula (P-1)

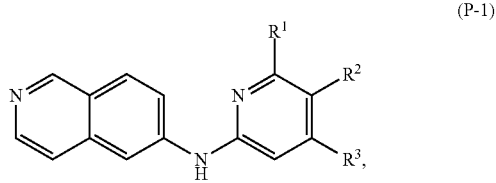

(P-1)

wherein
R$^2$ is methyl, R$^1$ is H and R$^3$ is selected from the group consisting of Br, —NO$_2$, —[N(CH$_3$)$_3$]$^+$, and 4-CH$_3$—Ph—SO$_2$—O;
or a pharmaceutically acceptable salt or a solvate thereof.

2. The compound according to claim 1, wherein the compound is

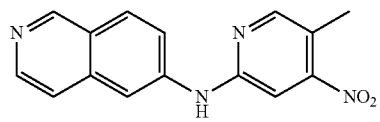 [SMILES: Cc1cnc(Nc2ccc3cnccc3c2)cc1[N+](=O)[O-]]

or a pharmaceutically acceptable salt or a solvate thereof.

* * * * *